United States Patent
Moorman et al.

(10) Patent No.: US 7,449,490 B2
(45) Date of Patent: *Nov. 11, 2008

(54) PHARMACEUTICALLY ACTIVE COMPOUNDS AND METHODS OF USE

(75) Inventors: Allan R. Moorman, Durham, NC (US); Romeo Romagnoli, Ferrara (IT); Pier Giovanni Baraldi, Ferrara (IT)

(73) Assignee: King Pharmaceuticals Research and Development, Inc., Cary, NC (US)

( * ) Notice: Subject to any disclaimer, the term of this patent is extended or adjusted under 35 U.S.C. 154(b) by 268 days.

This patent is subject to a terminal disclaimer.

(21) Appl. No.: 11/402,240

(22) Filed: Apr. 11, 2006

(65) Prior Publication Data

US 2006/0183921 A1  Aug. 17, 2006

Related U.S. Application Data

(62) Division of application No. 10/112,613, filed on Mar. 29, 2002, now Pat. No. 7,101,905.

(60) Provisional application No. 60/280,416, filed on Mar. 30, 2001.

(51) Int. Cl.
*A61K 31/381* (2006.01)
(52) U.S. Cl. ...................... 514/443; 514/438
(58) Field of Classification Search ................ 514/443, 514/288, 438
See application file for complete search history.

(56) References Cited

U.S. PATENT DOCUMENTS 7,101,905 B2 * 9/2006 Moorman et al. ........... 514/443

* cited by examiner

*Primary Examiner*—Charanjit S Aulakh
(74) *Attorney, Agent, or Firm*—Paivi Kukkola

(57) ABSTRACT

New fused thiophene compounds are provided and methods of using those compounds for a variety of therapeutic indications. Compounds of the invention are particularly useful for treatment of neuropathic pain.

9 Claims, No Drawings ial control in relation to the surrounding environment. A# PHARMACEUTICALLY ACTIVE COMPOUNDS AND METHODS OF USE This application is a division of U.S. application Ser. No. 10/112,613 filed Mar. 29, 2002 which claims the benefit of U.S. Provisional Application No. 60/280,416, filed on Mar. 30, 2001, hereby incorporated by reference in their entirety.

BACKGROUND TO THE INVENTION

1. Field of the Invention

The present invention relates to compounds useful in the normalization of a pathologically hyper-excited sensory nerve function in a conscious mammal, particularly a conscious human. In particular, the invention relates to new compounds particularly fused thiophene compounds, methods of synthesis for those compounds, and methods of using those compounds for reducing or eliminating hyper-excited sensory symptoms, such as neuropathic pain.

2. Background

Neuropathic pain is a persistent, chronic pain, generally described as a burning, shooting or lancinating sensation without obvious cause. These symptoms are often associated with damage to the nerves or nerve fibers. Sollevi (U.S. Pat. No. 5,691,318) has described the development of the hyper-excited sensory nerve function that would give rise to neuropathic pain. Generally, this involves some form of trauma, such as infection or mechanical lesion, inflicting damage upon the sensory nervous system.

The sensory nervous system mediates information from peripheral tissues and organs to the brain (CNS). The sensors in these peripheral tissues or organs are sensitive for such qualities as touch, increased or reduced temperature, vibration, pressure, smell, taste, balance, painful stimuli, vision, and hearing, and as such, is important to the subject's physiological control in relation to the surrounding environment. A disturbance of the nerves ability to transmit these sensory signals may lead to reduced sensory perception (hypoestesia) or to hyper-excitation in which there is increased sensory perception (the neuropathic condition). This neuropathic condition may be associated with decreased thresholds for touch and temperature (hyperesthesia), discomfort in the perception of touch or temperature (dysesthesia), discomfort or pain with touch, pressure, and/or thermal stimulation (allodynia), hypersensitivity to pain stimuli (hyperalgesia), balance disturbance, auditory disturbance (tinnitus), or ganglionic dysfunction. The neuropathic condition is generally considered chronic when persistent for 3 months or more.

In recent years, certain treatments for neuropathic pain have been proposed. One such approach has been a certain intrathecal (i.t.) administration of adenosine. When administered via a chronically implanted catheter into the cerebrospinal fluid of mice, Holmgren and coworkers (*Naunyn-Schmied. Arch. Pharmacol.* 334: 290-293, (1989)) reported a latency to the reflexive paw withdrawal provoked by a hot plate.

In humans with peripheral neuropathic pain, the slow intravenous infusion of adenosine (50-70 micrograms/kg/min) has been reported to alleviate spontaneous pain, relieve tactile allodynia, abolish thermal allodynia, and markedly attenuate hyperalgesia due to pinprick and pressure-induced allodynia. Although the duration of infusion was approximately 40-60 min, the effects were reported to last several hours (Sollevi et al., Pain 61: 155-158 (1995); Belfrage et al., *Anesth. Analg.* 81: 713-717 (1995); Sollevi, U.S. Pat. No. 5,691,318). In a later study, systemic adenosine administration was shown to reduce the area of dynamic tactile allodynia without signif cant improvement in spontaneous pain or tactile pain threshold. In some cases, the effect lasted several months (Sjolund et al., *Eur. J. Pain* 5: 199-207 (2001). Intravenous infusion of adenosine has been shown to reduce secondary hyperalgesia due to cutaneous inflammatory pain in humans (Sjolund et al., *Anesth. Analg.* 88: 605-610 (1999)).

Experimental data indicates that these effects of adenosine are mediated at the spinal level (Salter and Henry, *Neuroscience* 22: 631-650 (1987)). In a spinal nerve ligation model in rats, intrathecal adenosine produced a dose-dependent reduction in tactile allodynia lasting more than 24 hours (Lavand'homme and Eisenach, *Pain* 80: 31-36 (1999)). These effects were additive with intrathecal morphine and with the $\alpha_2$-adrenergic receptor agonist, clonidine (Gomes et al., *Anesthesiology* 91: 1072-1079 (1999)). Moreover, the effectiveness of intrathecal adenosine is reversed by the intrathecal administration of the adenosine $A_1$ receptor antagonist 8-cyclopentyl-1,3-diproyplxanthine, but not the adenosine $A_2$-preferential receptor antagonist 3,7-dimethyl-8-propargylxanthine, suggesting the involvement of the adenosine $A_1$ receptor in the mediation of neuropathic pain by adenosine (Gomes et al., *Anesthesiology* 91: 1072-1079 (1999)). Following intrathecal administration of 500-1000 micrograms of adenosine to humans with chronic neuropathic pain, both spontaneous and evoked pain was reduced in parallel with increased tactile pain thresholds in the allodynic areas and reduced areas of tactile hyperalgesia (Belfrage et al., *Anesth. Analg.* 89: 136-142 (1999)).

Attempts to modulate the metabolism of adenosine, thereby increasing the endogenous levels have also been examined. In rodents, the use of adenosine deaminase inhibitors to prevent the rapid deamination of adenosine to inosine was shown to greatly enhance the effectiveness of spinal morphine in reducing allodynia. A similar effect was observed with the intrathecal administration of nucleoside transport inhibitors which slow or prevent the cellular uptake of circulating adenosine. Adenosine kinase inhibitors, which prevent the phosphorylation of adenosine to adenosine monophosphate have also been reported as effective (Lynch et al., *Eur. J. Pharmacol.* 364: 141-146 (1999); Kowaluk et al., *J. Pharmacol. Exp. Ther.* 295: 1165-1174 (2000); Suzuki et al., *Br. J. Pharmacol.* 132: 1615-1623 (2001); Zhu et al., *Brain Res.* 905: 104-110 (2001)). All of these approaches act by increasing the concentration of adenosine available to the adenosine $A_1$ receptor.

Investigations of other modulation of adeonsine receptors have been reported in Bruns et al., *Mol. Pharmacol.* 38: 939-949 (1990); Bruns et al., *Mol. Pharmacol.* 38: 950-958 (1990); Bruns et al., *Mol. Pharmacol.* 38: 939-949, 950-958 (1990), Leung et al., *Naunyn-Schmied. Arch. Pharmacol.* 352: 206-212 (1995); Baraldi, U.S. Pat. No. 5,939,432; Baraldi et al., *Bioorg. Med. Chem. Lett.* 10: 1953-1957 (2000); van der Klein et al., *J. Med. Chem.* 42: 3629-3635 (1999); Kourounakis et al., *Drug Dev. Res.* 49: 227 237 (2000); and Tranberg et al., *J. Med. Chem.* 45: 382-389 (2002)).

SUMMARY OF THE INVENTION

We now provide compounds useful as allosteric modulators of the adenosine $A_1$ receptor and methods of preparation and use thereof are disclosed. Such compounds may be used in the normalization of a pathologically hyper-excited sensory nerve function in a mammal, particularly a conscious human.

More particularly, we now provide fused thiophene compounds that will be useful for a variety of therapeutic applications, including for pain management, particularly for treatment of neuropathic pain.

Fused thiophene compounds of the invention have at least one ring fused to a thiophene ring, preferably fused to the 3- and 4-thiophene carbon ring atoms. By stating that a ring is "fused" to the thiophene moiety of the thiophene compound, it is meant that two or more of the thiophene moiety ring atoms (typically carbon atoms) are additionally part of a further ring structure. As referred to herein, "thiophene moiety" refers to the 5-membered thiophene ring to which one or more additional rings may be fused. Those two thiophene moiety ring atoms taken together preferably are adjacent ring atoms, particularly 3- and 4-thienyl ring atoms. Preferred fused thiophene compounds will have one or more non-hydrogen ring substituents.

Preferred rings fused to the thiophene moiety are carbon alicyclic rings (i.e. a non-aromatic ring having only carbon ring atoms). That ring fused to the thiophene moiety is typically substituted, preferred substituition patterns include a further fused ring, which suitably is an aromatic ring such as a fused carbocyclic aryl group especially a fused phenyl group.

Preferably, the 5-position of the thiophene ring is substituted by an amine group, particularly to provide a primary amine (i.e. —NH$_2$) or a secondary amine or tertiary amine group that can generate a primary amine in vivo, i.e. an amine having at least one metabolically cleavable substituents such as an acetyl or other alkanoyl group, a sacharride group, or the like.

In certain preferred aspects of the invention, the fused thiophene compound has a substantially coplanar structure. Such co-planarity may be suitably provided by appropriate substitution of the ring fused to the thiophene moiety, e.g. by a fused ring that has a carbonyl (i.e. C═O) ring atom, or at least one endocyclic carbon-carbon double bond. A polar group such as carbonyl moiety also can interact (e.g. H-bonding) with the preferred amino substituents of the thienyl moiety, thereby further promoting a substantially coplanar structure.

In further aspects of the invention, the thiophene compound may comprise at least one additional ring structure, preferably a non-aromatic ring linking the thiophene ring and the ring fused thereto, e.g. as may be provided by an optionally substituted alkylene or heteroalkylene chain that links the 2-thiophene ring atom to a ring fused at 3,4-thiphene ring positions. Suitably, such an alkylene or heteroalkylene chain will have 3, 4, 5, 6, or 7 atoms in the chain, more typically 3, 4 or 5 chain atoms.

Preferred fused thiophene compounds of the invention include those of the following Formulae (I), (II), (III) and (IV):

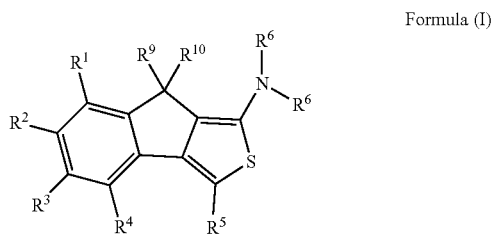

Formula (I)

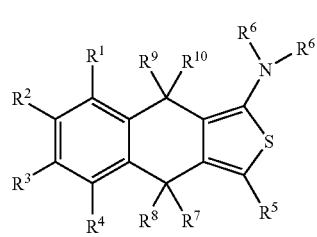

Formula (II)

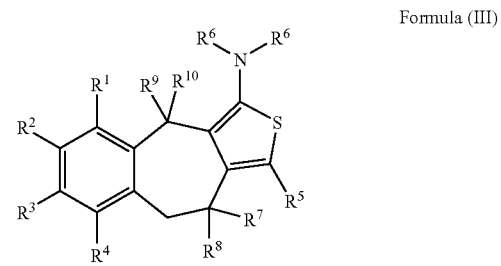

Formula (III)

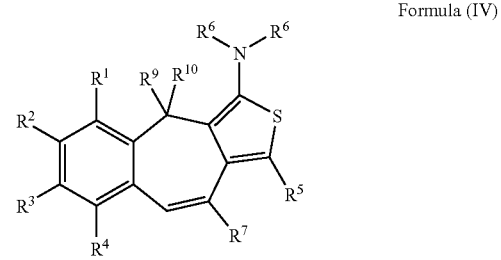

Formula (IV)

wherein $R^1$, $R^2$, $R^3$, and $R^4$ are independently hydrogen, halogen, cyano, amino, nitro, thio, optionally substituted alkyl preferably having 1 to about 20 carbon atoms, optionally substituted alkenyl preferably having 2 to about 20 carbon atoms, optionally substituted alkynyl preferably having 2 to about 20 carbon atoms, optionally substituted alkoxy preferably having 1 to about 20 carbon atoms, optionally substituted alkylamino preferably having 1 to about 20 carbon atoms, optionally substituted dialkylamino preferably having independently selected alkyl groups where each alkyl group having 1 to about 20 carbon atoms, optionally substituted alkylthio preferably having 1 to about 20 carbon atoms, optionally substituted alkylsulfinyl preferably having 1 to about 20 carbon atoms, optionally substituted alkylsulfonyl preferably having 1 to about 20 carbon atoms, optionally substituted alkanoyl preferably having 1 to about 20 carbon atoms, optionally substituted carbocyclic aryl, or an optionally substituted heteroalicyclic or heteroaromatic preferably having from 1 to 3 rings and from 1 to 3 N, O or S atoms in each ring;

$R^5$ is hydrogen, optionally substituted alkyl preferably having 1 to about 20 carbon atoms, optionally substituted alkenyl preferably having 2 to about 20 carbon atoms, optionally substituted alkynyl preferably having 2 to about 20 carbon atoms, optionally substituted carbocyclic aryl, or an optionally substituted heteroalicyclic or heteroaromatic preferably having from 1 to 3 rings and from 1 to 3 N, O or S atoms in each ring;

each $R^6$ is independently hydrogen or a metabolically cleavable group, and preferably at least one or both $R^6$ are hydrogen;

$R^7$ is hydrogen, optionally substituted alkyl preferably having 1 to about 20 carbon atoms, optionally substituted alkenyl preferably having 2 to about 20 carbon atoms, optionally substituted alkynyl preferably having 2 to about 20 carbon atoms; or $R^7$ and $R^5$ taken together with the carbon atoms to which they are attached form a five, six, or seven-membered carbon alicyclic or heteroalicyclic ring;

$R^8$ is hydrogen or optionally substituted alkyl preferably having 1 to about 12 carbon atoms; and $R^9$ and $R^{10}$ are independently hydrogen or hydroxyl, or together may represent a carbonyl oxygen; and pharmaceutically acceptable salt thereof.

Preferred compounds of the invention exhibit good activity in an $A_1$-adenosine receptor cAMP enhancement assay, as such assay is exemplified in Example 34, which follows. References herein to a "cAMP enhancement assay" are defined to mean the assay of the protocol specified in Example 34 which follows. Particularly preferred compounds will provide a 10 percent increase in cAMP activity relative to control at a test compound concentration of 10 µM in such a defined cAMP enhancement assay, more preferably a 30 or 40 percent increase in cAMP activity relative to control at a test compound concentration of 10 µM.

The invention further provides therapeutic methods, particularly methods for treating a mammal suffering from or susceptible to (prophylactic therapy) to chronic pain particularly neuropathic pain; a cardiac disease or disorder including congestive heart failure and cardiac disarrhythmias such as paroxysmal supraventricular tachycardia; neurological disease or injury; sleep disorders; diabetes; and various inflammatory conditions. The therapeutic methods of the invention in general comprise administering to a mammal, such as a primate particularly a human, a therapeutically effective amount of a fused thiophene compound, such as a compound of the above Formulae (I), (II), (III) or (IV) as well as any of Formulae (V) through (IX) as those formulae are defined below.

Therapeutic methods of the invention in general comprise administering an effective amount of one or more fused thienyl compounds as disclosed herein to a mammal in need thereof, particularly a primate such as a human. Preferred fused thienyl compounds include those of Formulae (I) through (IX) as those formulae are defined herein.

In a further aspect, the invention provides use of a fused thiophene compound, including a compound of any one of Formulae (I) through (IX) for the treatment or prevention (including prophylactic treatment) of a disease or condition as disclosed herein, including chronic pain particularly neuropathic pain; a cardiac disease or disorder including congestive heart failure and cardiac disarrhythmias such as paroxysmal supraventricular tachycardia; neurological disease or injury; sleep disorders; diabetes; or various inflammatory conditions.

In a yet further aspect, the invention provides use of a fused thiophene compound, including a compound of any one of Formulae (I) through (IX) for the preparation of a medicament for the treatment or prevention (including prophylactic treatment) of a disease or condition as disclosed herein, including chronic pain, particularly neuropathic pain; a cardiac disease or disorder including congestive heart failure and cardiac disarrhythmias such as paroxysmal supraventricular tachycardia; neurological disease or injury; sleep disorders; diabetes; or various inflammatory conditions.

Preferred methods of the invention include identifying and/or selecting a subject (e.g. mammal, particularly human) that is susceptible to or suffering from a condition disclosed herein, and thereafter administering to the identified and/or selected subject one or more fused thiophene compounds of the invention such as a compound of any one of Formulae (I) through (IX), particularly a subject that is identified and/or selected as being susceptible to or suffering from a disease or condition as disclosed herein, including chronic pain particularly neuropathic pain; a cardiac disease or disorder including congestive heart failure and cardiac disarrhythmias such as paroxysmal supraventricular tachycardia; neurological disease or injury; sleep disorders; diabetes; or various inflammatory conditions.

Pharmaceutical compositions also are provided comprising a therapeutically effective amount of one or more fused thiophene compounds of the Formulae (I) though (IX) as those formulae are defined herein typically together with a pharmaceutically acceptable carrier.

Other aspects of the invention are disclosed infra.

DETAILED DESCRIPTION OF THE INVENTION

As discussed above, we have now found fused thiophene compounds useful in the normalization of a pathologically hyper-excited sensory nerve function in a conscious mammal, particularly a conscious human. Compounds of the invention are particularly useful for pain management, especially treatment or prophylaxis of neuropathic pain.

Preferred compounds of the invention are fused thiophene compounds that comprise 3 or 4 fused rings, preferably including a non-aromatic ring fused to a thiophene moiety at the 3 and 4-thiophene ring positions, and a further aromatic ring such as phenyl fused to that non-aromatic ring. A further ring suitably may link the thienyl group and the interposed non-aromatic ring.

All of the available ring positions of the fused thiophene may be optionally substituted by a group other than hydrogen, including by groups such as halogen, $C_{1-6}$alkyl, $C_{1-6}$alkoxy, $C_{1-6}$alkylamino, carbocyclic aryl such as phenyl and the like. Preferably, the 5-position of the thiophene ring is substituted by an amine group, particularly to provide a primary amine (i.e. —$NH_2$) or an amine that can generate a primary amine in vivo e.g. where the amine is substituted by one or more metabolically cleavable groups such as acetyl, a sugar such as a saccharine, carbamate, ester, or the like. Preferably, the interposed non-aromatic ring has substitution that provides substantial co-planarity of the compound, e.g. as may be provided by a carbonyl ring atom or an endocyclic carbon-carbon double bond.

Particularly preferred compounds of the invention include those of the following Formulae:

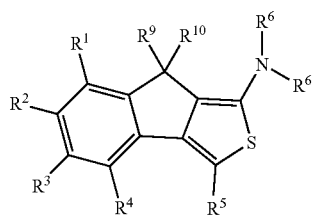

Formula (I)

-continued

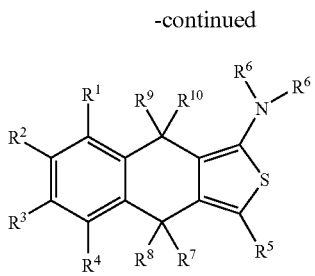
Formula (II)

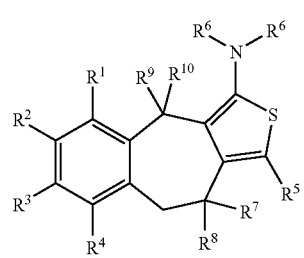
Formula (III)

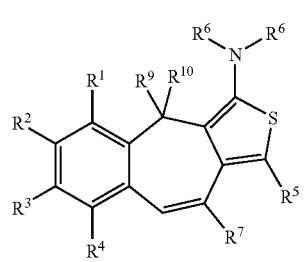
Formula (IV)

wherein

R$^1$ through R$^{10}$ are as specified above; and pharmaceutically salts of such compounds.

Preferred compounds of the invention also include those of the following Formulae (V), (VI), (VII), (VII), and (IX):

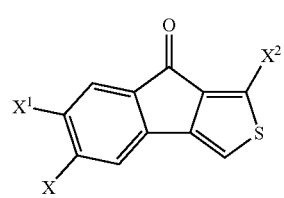
Formula (V)

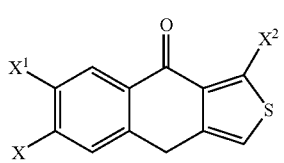
Formula (IV)

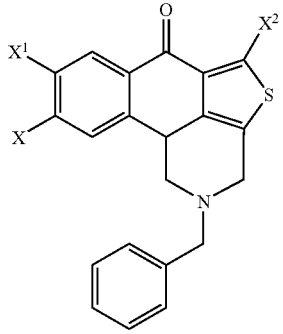
Formula (VII)

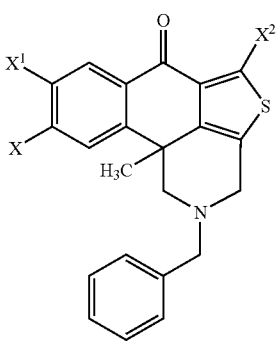
Formula (VIII)

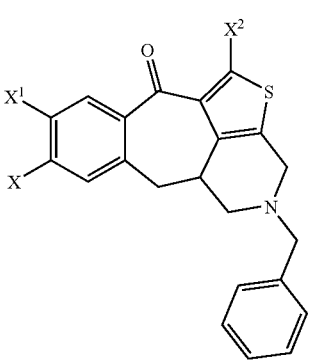
Formula (IX)

wherein

X and X$^1$ are independently H, optionally substituted alkyl preferably having 1 to about 20 carbon atoms, optionally substituted alkenyl preferably having 2 to about 20 carbon atoms, optionally substituted alkynyl preferably having 2 to about 20 carbon 10 atoms, optionally substituted alkoxy preferably having 1 to about 20 carbon atoms, optionally substituted carbocyclic aryl, nitro, halogen, or isotopic analogues thereof; and X$^2$ is amino, substituted amino, disubstituted amino or acylated amine.

Specifically preferred compounds of the invention include the following and pharmaceutically acceptable salts of such compounds:

1-amino-8H-indeno[1,2-c]thiophen-8-one;
1-amino-5-chloro-8H-indeno[1,2-c]thiophen-8-one;
1-amino-5-methyl-8H-indeno[1,2-c]thiophen-8-one;
1-amino-4,5-dichloro-8H-indeno[1,2-c]thiophen-8-one;

1-amino-4,5-dimethyl-8H-indeno[1,2-c]thiophen-8-one;
1-amino-5-ethyl-8H-indeno[1,2-c]thiophen-8-one;
1-amino-5-propyl-8H-indeno[1,2-c]thiophen-8-one;
3-aminonaphtho[2,3-c]thiophen-4(9H)-one;
3-amino-6-chloronaphtho[2,3-c]thiophen-4(9H)-one;
3-amino-6-methylnaphtho[2,3-c]thiophen-4(9H)-one;
3-amino-6,7-dichloronaphtho[2,3-c]thiophen-4(9H)-one;
3-amino-6,7-dimethylnaphtho[2,3-c]thiophen-4(9H)-one;
3-amino-6-ethylnaphtho[2,3-c]thiophen-4(9H)-one;
3-amino-6-propylnaphtho[2,3-c]thiophen-4(9H)-one;
5-amino-2-benzyl-1,2,3,10b-tetrahydro-6H-benzo[h]thieno[2,3,4-de]isoquinolin-6-one;
5-amino-2-benzyl-9-chloro-1,2,3,10b-tetrahydro-6H-benzo[h]thieno[2,3,4-de]isoquinolin-6-one;
5-amino-2-benzyl-9-methyl-1,2,3,10b-tetrahydro-6H-benzo[h]thieno[2,3,4-de]isoquinolin-6-one;
5-amino-2-benzyl-8,9-dichloro-1,2,3,10b-tetrahydro-6H-benzo[h]thieno[2,3,4-de]isoquinolin-6-one;
5-amino-2-benzyl-8,9-dimethyl-1,2,3,10b-tetrahydro-6H-benzo[h]thieno[2,3,4-de]isoquinolin-6-one;
5-amino-2-benzyl-9-ethyl-1,2,3,10b-tetrahydro-6H-benzo[h]thieno[2,3,4-de]isoquinolin-6-one;
5-amino-2-benzyl-9-propyl-1,2,3,10b-tetrahydro-6H-benzo[h]thieno[2,3,4-de]isoquinolin-6-one;
5-amino-2-benzyl-10b-methyl-1,2,3,10b-tetrahydro-6H-benzo[h]thieno[2,3,4-de]isoquinolin-6-one;
5-amino-2-benzyl-9-chloro-10b-methyl-1,2,3,10b-tetrahydro-6H-benzo[h]thieno[2,3,4-de]isoquinolin-6-one;
5-amino-2-benzyl-9,10b-dimethyl-1,2,3,10b-tetrahydro-6H-benzo[h]thieno[2,3,4-de]isoquinolin-6-one;
5-amino-2-benzyl-8,9-dichloro-10b-methyl-1,2,3,10b-tetrahydro-6H-benzo[h]thieno[2,3,4-de]isoquinolin-6-one;
5-amino-2-benzyl-8,9,10b-trimethyl-1,2,3,10b-tetrahydro-6H-benzo[h]thieno[2,3,4-de]isoquinolin-6-one;
S-amino-2-benzyl-9-ethyl-10b-methyl-1,2,3,10b-tetrahydro-6H-benzo[h]thieno[2,3,4-de]isoquinolin-6-one;
S-amino-2-benzyl-9-propyl-10b-methyl-1,2,3,10b-tetrahydro-6H-benzo[h]thieno[2,3,4-de]isoquinolin-6-one;
1-amino-4-benzyl-4,5,5a,6-tetrahydro-2-thia-4-azadibenzo[cd,g]azulen-11(3H)-one;
1-amino-4-benzyl-8-chloro-4,5,5a,6-tetrahydro-2-thia-4-azadibenzo[cd,g]azulen-11(3H)-one;
1-amino-4-benzyl-8-methyl-4,5,5a,6-tetrahydro-2-thia-4-azadibenzo[cd,g]azulen-11(3H)-one;
1-amino-4-benzyl-8,9-dichloro-4,5,5a,6-tetrahydro-2-thia-4-azadibenzo[cd,g]azulen-11(3H)-one;
1-amino-4-benzyl-8,9-dimethyl-4,5,5a,6-tetrahydro-2-thia-4-azadibenzo[cd,g]azulen-11(3H)-one;
1-amino-4-benzyl-8-ethyl-4,5,5a,6-tetrahydro-2-thia-4-azadibenzo[cd,g]azulen-11(3H)-one;
1-amino-4-benzyl-8-propyl-4,5,5a,6-tetrahydro-2-thia-4-azadibenzo[cd,g]azulen-11(3H)-one;
1-amino-2-thia-cyclopenta[a]inden-8-one;
1-amino-7-methyl-2-thia-cyclopenta[a]inden-8-one;
1-amino-5-methyl-2-thia-cyclopenta[a]inden-8-one;
1-amino-7-chloro-2-thia-cyclopenta[a]inden-8-one;
1-amino-5-chloro-2-thia-cyclopenta[a]inden-8-one;
1-amino-6,7-dichloro-2-thia-cyclopenta[a]inden-8-one;
1-amino-5,6-dichloro-2-thia-cyclopenta[a]inden-8-one;
1-amino-4-chloro-2-thia-cyclopenta[a]inden-8-one;
1-amino-6-chloro-2-thia-cyclopenta[a]inden-8-one;
1-amino-4-methyl-2-thia-cyclopenta[a]inden-8-one;
1-amino-6-methyl-2-thia-cyclopenta[a]inden-8-one;
1-amino-6-ethyl-2-thia-cyclopenta[a]inden-8-one;
1-amino-4-methoxy-2-thia-cyclopenta[a]inden-8-one;
1-amino-5-methoxy-2-thia-cyclopenta[a]inden-8-one;
1-amino-7-methoxy-2-thia-cyclopenta[a]inden-8-one;
1-amino-6-methoxy-2-thia-cyclopenta[a]inden-8-one;
3-amino-6-chloro-naphtho[2,3-c]thiophen-4(9H)-one;
3-amino-8-chloro-naphtho[2,3-c]thiophene-4(9H)-one; and
1,6-diamino-2-thia-cyclopenta[a]inden-8-one;

or a pharmaceutically acceptable salt thereof.

As used herein, the term "alkyl" refers to monovalent straight, branched, or cyclic alkyl groups preferably having from 1 to 20 carbon atoms, more preferably 1 to 10 carbon atoms, and most preferably 1 to 6 carbon atoms ("lower alkyl"). This term is exemplified by groups such as methyl, ethyl, n-propyl, iso-propyl, n-butyl, iso-butyl, n-hexyl, 2-methylpropyl, 3-methylbutyl, and the like. The terms "alkylene" and "lower alkylene" refer to divalent radicals of the corresponding alkane. Further, as used herein, other moieties having names derived from alkanes, such as alkoxy, alkanoyl, alkenyl, cycloalkenyl, etc., when modified by "lower," have carbon chains of ten or fewer carbon atoms. In those cases where the minimum number of carbons required are greater than one, e.g., alkenyl and alkynyl (minimum of two carbons) and cycloalkyl (minimum of three carbon atoms), it is to be understood that the term "lower" means at least the minimum number of carbon atoms.

As indicated above, alkyl groups may be substituted e.g. by having from 1 to 5 substituents, and preferably from 1 to 3 substituents, suitably selected from the group consisting of alkoxy, substituted alkoxy, cycloalkoxy, substituted cycloalkoxy, cycloalkyl, substituted cycloalkyl, cycloalkenyl, substituted cycloalkenyl, alkynyl, substituted alkynyl, acyl, amino, aryl, substituted aryl, carboxyl, carboxyalkyl, cyano, fluoro, hydroxyl, halogen, heteroaryl, heterocyclic, nitro, alkylthio, thiol, mono(alkyl)amino, di(alkyl)amino, mono(substituted alkyl)amino, di(substituted alkyl)amino, unsymmetric disubtituted amines having different substitutents selected from alkyl, substituted alkyl, aryl, substituted aryl, aralkyl, and substituted aralkyl, —SO-alkyl, —SO-substituted alkyl, —SO-aryl, —SO-substituted aryl, —SO$_2$-alkyl, —SO$_2$-substituted alkyl, —SO$_2$-aryl, and —SO$_2$-substituted aryl. As used herein, other moieties having the prefix "substituted" are intended to include one or more of the substituents listed above.

As used herein, the term "alkenyl" refers to straight or branched alkenyl groups having from 2 to 20, more preferably from 2 to 10 carbon atoms, and most preferably 2 to 6 carbons atoms, and having at least 1 and preferable from 1 to 3 sites of alkenyl unsaturation. This term is exemplified by groups such as ethenyl(CH=CH$_2$), 1-propenyl(CH=CH—CH$_3$), 2-propenyl(C(CH$_3$)=CH$_2$), 3-methyl-2-pentenyl(CH$_2$—CH=C(CH$_3$)—CH$_2$CH$_3$), and the like.

As used herein, the term "alkynyl" refers to straight or branched alkynyl groups having from 2 to 20 carbon atoms, more preferably from 2 to 10 carbon atoms, and most preferably from 2 to 6 carbon atoms, and having at least 1 and preferably from 1 to 2 sites of alkynyl unsaturation. This term is exemplified by groups such as ethynyl, 1-propynyl, 2-propynyl, 2-butynyl, 4,4-dimethyl-2-pentynyl, and the like.

As used herein, the term "cycloalkyl" refers to cyclic alkyl groups of from 3 to 20 carbon atoms having a single cyclic ring or multiple rings joined in either a fused or spirocyclic condensation. This term is exemplified by groups such as cyclopropyl, cyclopentyl, cyclohexyl, cyclooctyl, norbornyl, perhydrofluorenyl, adamantyl, and the like. As indicated, the term alkyl is inclusive of cycloalkyl unless otherwise indicated.

As used herein, the term "cycloalkenyl" refers to cyclic alkenyl groups of from 1 to 20 carbon atoms having a single cyclic ring or multiple rings joined in either a fused or spirocyclic condensation and having at least 1 and preferably from 1 to 2 sites of alkenyl unsaturation. This term is exemplified by groups such as cyclopentenyl, cycloheptenyl, 1,3-cyclooctadienyl, cycloheptatrienyl, bicyclo[2.2.1]hepta-2,5-dienyl, and the like.

The term "carbon alicyclic group" refers to structures where each ring member is carbon and the group is non-aromatic, although the group may have one or more endocyclic carbon-carbon double bonds. Preferred carbon alicyclic groups have 5, 6, 7 or 8 ring atoms, more preferred 5, 6 or 7 ring atoms.

As used herein, the term "aryl" or "carbocyclic aryl" refers to an unsaturated, aromatic, carbocyclic group of from 6 to 20 carbon atoms having a single ring or multiple condensed rings. This term is exemplified by groups such as phenyl, 1-naphthyl, 2-naphthyl, anthracenyl, 1,2-benzanthracenyl, and the like. As used herein, the term "aryl" also refers to those fused-ring hydrocarbons in which the aromatic ring or rings are condensed to additional non-aromatic rings. In this manner, this term is exemplified by groups such as fluorenyl, acenaphthenyl, biphenylenyl, fluoranthenyl, and the like. Unless otherwise constrained by the definition for the aryl substituent, such aryl groups can optionally be substituted with from one to five substituents, preferably one to three substituents, selected from the list given herein.

As used herein, the term "aralkyl" refers to an aryl or substituted aryl group, attached to an alkylene group or substituted alkylene group, where aryl, substituted aryl, alkylene, and substituted alkylene are as defined herein.

As used herein, the term "heteroalicyclic" refers to a monovalent saturated or unsaturated carbocyclic group having a single ring or multiple condensed rings, from 1 to 15 carbon atoms and from 1 to 5 heteroatoms within the ring or rings, preferably from 1 to 9 carbon atoms and from 1 to 4 heteroatoms within the ring or rings, selected from the group of heteroatoms consisting of nitrogen, sulfur, and oxygen. This term is exemplified by groups such as tetrahydrofuranyl, pyrrolinyl, pyrrolidinyl, oxazolidinyl, thiazolidinyl, imidazolinyl, imidazolidinyl, piperidinyl, piperazinyl, quinuclidinyl, thiomorpholinyl, morpholinyl, dioxolanyl, and the like.

As used herein, the term "heteroaromatic" refers to a 5-membered or 6-membered heterocyclic, aromatic group, which can optionally be fused to an aryl or substituted aryl ring, where heterocyclic, aryl, and substituted aryl are as defined herein. This term is exemplified by groups such as pyrrolyl, furanyl, thiophenyl, pyrazolyl, imidazolyl, isoxazolyl, oxazolyl, isothiazolyl, thiazolyl, thiadiazolyl, triazolyl, tetrazolyl, pyridyl, pyridazyl, pyrimidyl, indolyl, benzofuranyl, benzotriazolyl, quinolinyl, isoquinolinyl, and the like. Optionally, the heteroaryl group may be fused to a second or third heteroaryl group. In this context, this term is exemplified by groups such as 1,2,3-triazolo[4,5-B]pyridinyl, s-triazolo[1,5-A]pyrimidinyl, pyrazolo[3,4-D]pyrimidinyl, purinyl, pterinyl, pteridinyl, pyrimido[5,4-D]pyrimidinyl, and the like.

As used herein, the term "alkanoyl" refers to the groups alkyl-C(O)—, substituted alkyl-C(O)—, cycloalkyl-C(O)—, substituted cycloalkyl-C(O)—, aryl-C(O)—, substituted aryl-C(O)—, heterocyclic-C(O)—, and heteroaryl-C(O)—, where alkyl, substituted alkyl, cycloalkyl, substituted cycloalkyl, aryl, substituted aryl, heterocyclic, and heteroaryl are as defined herein.

As used herein, the term "alkoxy" refers to the group "alkyl-O—", "substituted alkyl-O—", "cycloalkyl-O—", or "substituted cycloalkyl-O—" where alkyl, substituted alkyl, cycloalkyl, and substituted cycloalkyl are as defined herein. This term is exemplified by such groups as methoxy, ethoxy, 1-propoxy, 2-propoxy, 1-butyloxy, tert-butyloxy, cyclopentyloxy, cyclohexylethoxy, and the like.

As used herein, the term "halo" or "halogen" refers to fluoro, chloro, bromo, and iodo groups.

Heteroalkylene groups typically will have about 1 to about 8 atoms in the chain, more typically 1 to about 6 atoms in the linkage and at least one hetero atom (N, O or S) as a divalent chain member. As the terms "heteroalkylene" and "alkylene" are used herein, such chains may have one or more double or triple bonds in the chain, i.e. the term heteroalkylene is inclusive of heteroalkenylene and heteroalkynylene groups, and the term alkylene is inclusive of heteroalkenylene and heteroalkynylene groups.

Alkylthio groups of compounds of the invention suitably having one or more thioether linkages, typically 1, 2 or 3 thioether linkages, and preferably 1 to about 12 carbon atoms, more preferably 1 to about 6 carbon atoms.

Alkylsulfinyl groups of compounds of the invention suitably having one or more sulfinyl-S(O)— groups, typically 1, 2 or 3 sulfinyl linkages, and preferably 1 to about 12 carbon atoms, more preferably 1 to about 6 carbon atoms.

Alkylsulfonyl groups of compounds of the invention suitably having one or more sulfonyl-S(O)$_2$— groups, typically 1, 2 or 3 S(O)$_2$ linkages, and preferably 1 to about 12 carbon atoms, more preferably 1 to about 6 carbon atoms.

Preferred alkylamino groups of compounds of the invention include those that have one or more primary, secondary and/or tertiary amine groups, preferably 1, 2 or 3 total amine groups, and from 1 to about 12 carbon atoms, more preferably 1 to about 6 carbon atoms.

The term "metabolically cleavable group" as used herein denotes a group which can be cleaved in vivo upon administration to a subject, particularly to provide a primary amine. Examples of metabolically cleavable groups include optionally substituted $C_{1-8}$alkyl such as methyl, acetyl and other alkanoyl groups preferably optionally substituted $C_{1-6}$alkanoyl, ethoxycarbonyl, benzoyl, alkoxymethyl, lactates, sugar groups, and the like.

As indicated, various substituents in compounds of the invention including compounds of Formulae (I) through (IX) may be optionally substituted. Suitable group that may be present on a "substituted" substituent include halogen (F, Cl, Br or I); cyano; hydroxyl; nitro; alkanoyl, e.g., $C_{1-6}$alkanoyl group such as acetyl and the like; alkyl groups, e.g., $C_{1-6}$alkyl; alkoxy groups, e.g., $C_{1-6}$alkoxy; alkylsulfinyl such as groups having from 1 to about 6 carbon atoms; alkylsulfonyl such as groups having 1 to about 6 carbon atoms; alkylamino such as groups having from 1 to about 6 carbon atoms; carbocyclic aryl such as phenyl and naphthyl; heteroalicyclic such as those discussed above; or heteromatic typically having 1, 2 or 3 N, O or S ring atoms. A "substituted" substituent of a compound of the invention may be substituted at one or more available positions, typically 1, 2 or 3 positions, by one or more suitable groups such as those listed immediately above.

As to any of the above groups that contain one or more substituents, it is understood by those skilled in the art, that such groups do not contain any substitution or substitution patterns which are sterically unfeasible and/or synthetically impractical.

The compounds of the present invention may be synthesized by a variety of routes. However, the 1-amino-2-thia-cyclopenta[a]inden-8-one derivatives of Formula (Ia), shown below, are preferably synthesized by a Knoevenagel condensation of a suitably substituted acetophenone with ethyl cyanoacetate to prepare the intermediate 3-aryl-2-cyano-but-2-enoic esters (Scheme I below). Reaction of the Knoevenagel adducts with elemental sulfur in a Gewald reaction was found to afford the requisite 2-amino-4-aryl-thiophene-3-carboxylic acid esters. Protection of the amine, followed by saponification of the ester, and Friedel-Crafts cyclization was shown to provide the protected 1-amino-2-thia-cyclopenta[a]inden-8-ones that were readily deprotected under conditions widely known to those skilled in the art. Similarly, the 1-amino-2-thia-cyclopenta[a]naphthalene-9-one derivatives of Formula (IIa), shown below, are preferably synthesized through the expediency of a Knoevenagel condensation of ethyl cyanoacetate and an appropriately substituted methyl benzyl ketone (Scheme II below). Gewald reaction of the Knoevenagel adducts provides the corresponding 2-amino-4-arylmethyl-thiophene-3-carboxylic acid esters. Protection of the amine, followed by saponification of the ester affords the intermediate 2-(protected)-amino-4benzylthiophene-3-carboxylic acids. Cyclization in a Friedel-Crafts procedure, followed by deprotection of the amine, would afford the desired products.

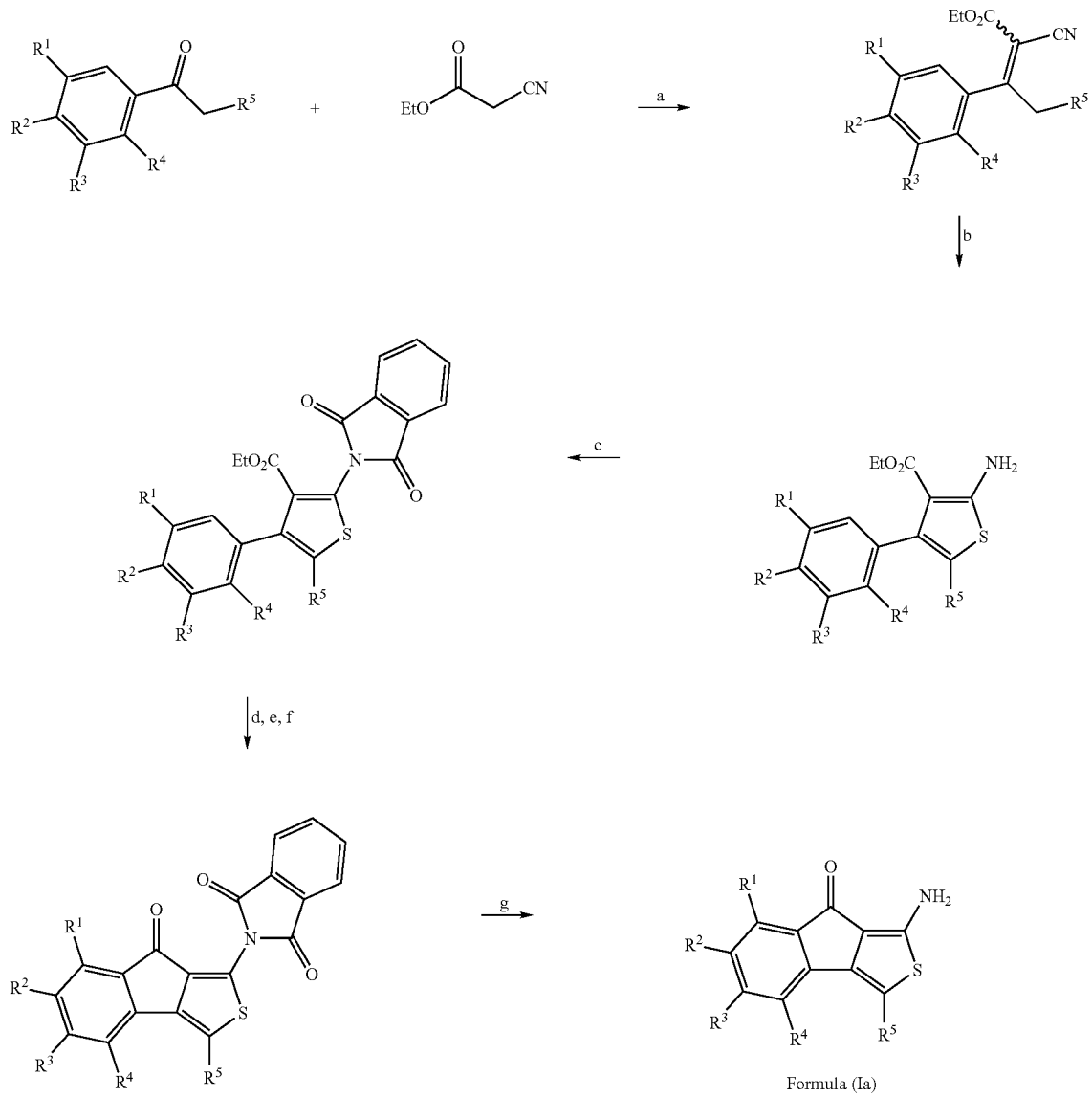

a. $CH_3CO_2^-NH_4^+$, $CH_3CO_2H$, benzene; b. morpholine, $S_8$, ethanol; c. phthalic anhydride, acetic acid; d. NaOH; e. $SOCl_2$; f. $AlCl_3$, $CH_2Cl_2$; g. $NH_2NH_2 \cdot H_2O$.

Scheme II:

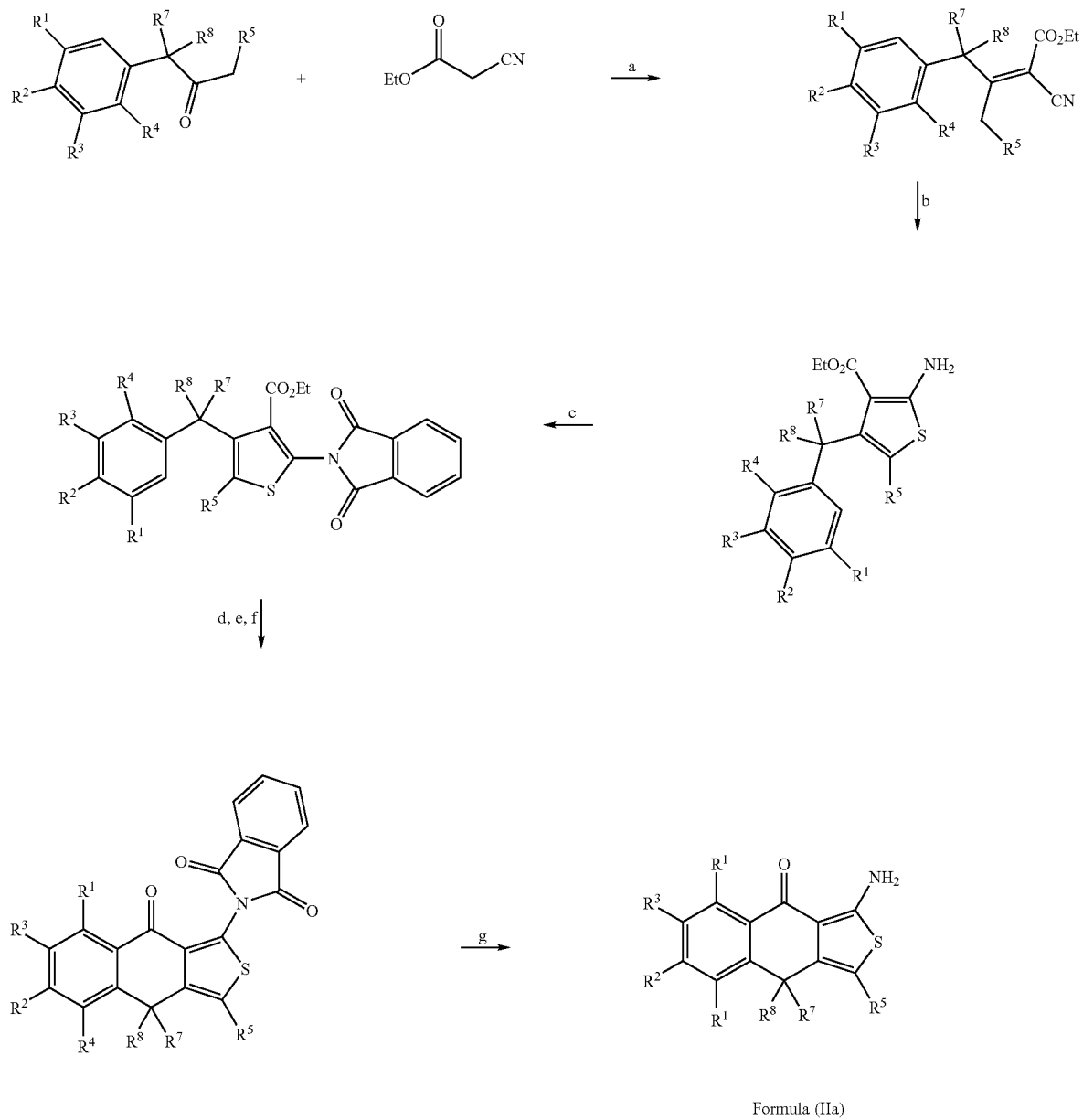

a. CH₃CO₂⁻NH₄⁺, CH₃CO₂H, benzene; b. morpholine, S₈, ethanol; c. phthalic anhydride, acetic acid; d. NaOH; e. SOCl₂; f. AlCl₃, CH₂Cl₂; g. NH₂NH₂·H₂O.

In similar fashion, compounds of Formula (IIIa) and Formula (IVa) as defined below are synthesized from the corresponding 4-phenyl-2-butanones and 4-phenyl-3-buten-2-ones, respectively. For example, Knoevenagel of the requisite 4-phenyl-2-butanone with ethyl cyanoacetate affords the desired 3-alkyl-5-aryl-2-cyano-2-pentenoic acid esters (Scheme III below). Preferentially, such intermediates will contain one or two substituents at the 3-position, which optionally may serve only to mask the methylene, being removed at a later stage of the synthesis. Application of the Gewald reaction to this Knoevenagel adduct provides the desired 2-amino-3-arylethyl-thiophene-3-carboxylic acid esters. As with the compounds described in Schemes I and II, protection of the amine, saponification of the ester, followed by Friedel-Crafts cyclization affords the requisite intermediate that is readily deprotected using conditions widely known to those skilled in the art, affording the corresponding 3-amino-9,10-dihydro-2-thia-benzo[f]azulen-4-ones of Formula (IIIa) below.

Scheme III:
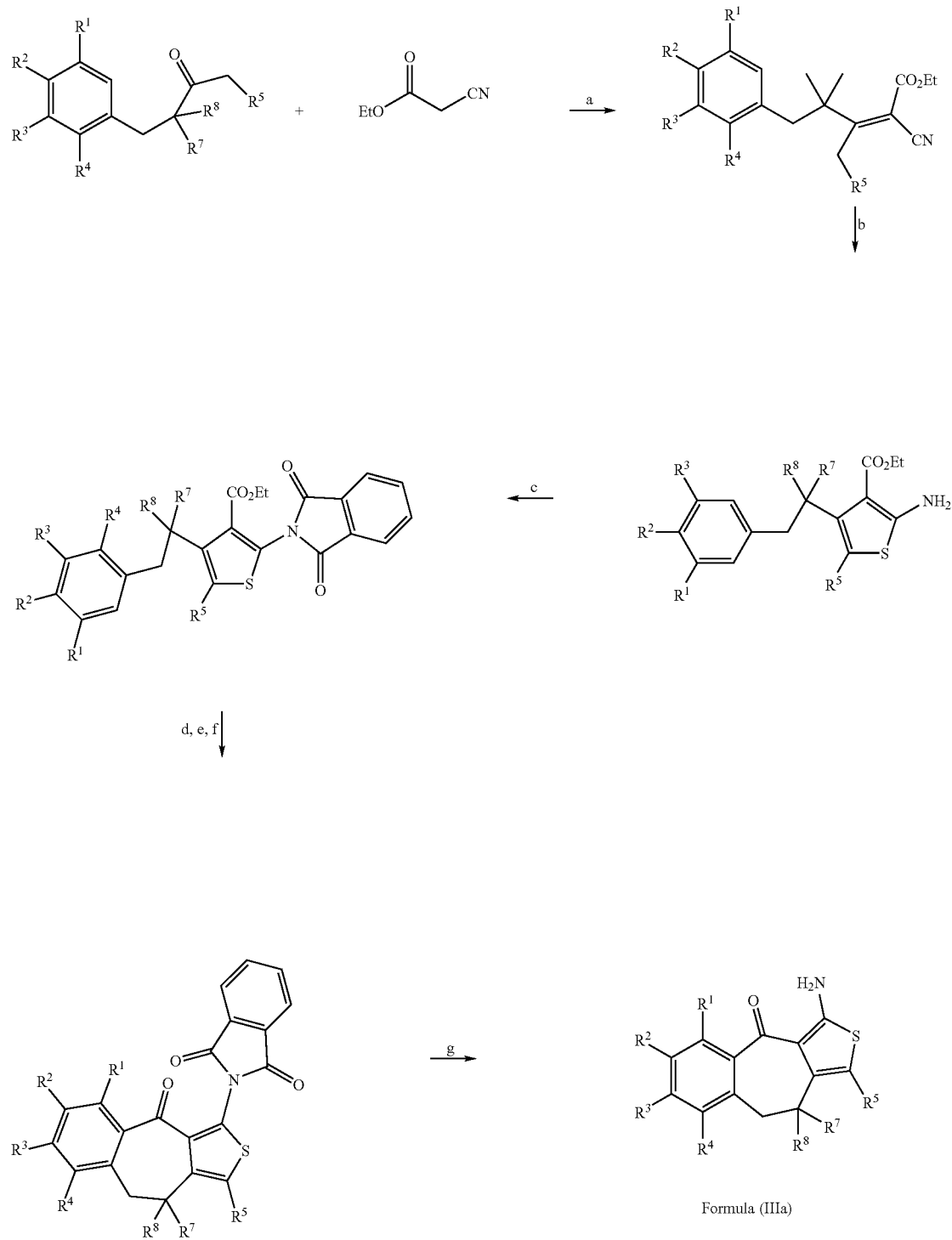
a. $CH_3CO_2^-NH_4^+$, $CH_3CO_2H$, benzene; b. morpholine, $S_8$, ethanol; c. phthalic anhydride, acetic acid; d. NaOH; e. $SOCl_2$; f. $AlCl_3$, $CH_2Cl_2$; g. $NH_2NH_2 \cdot H_2O$.

Scheme IV:

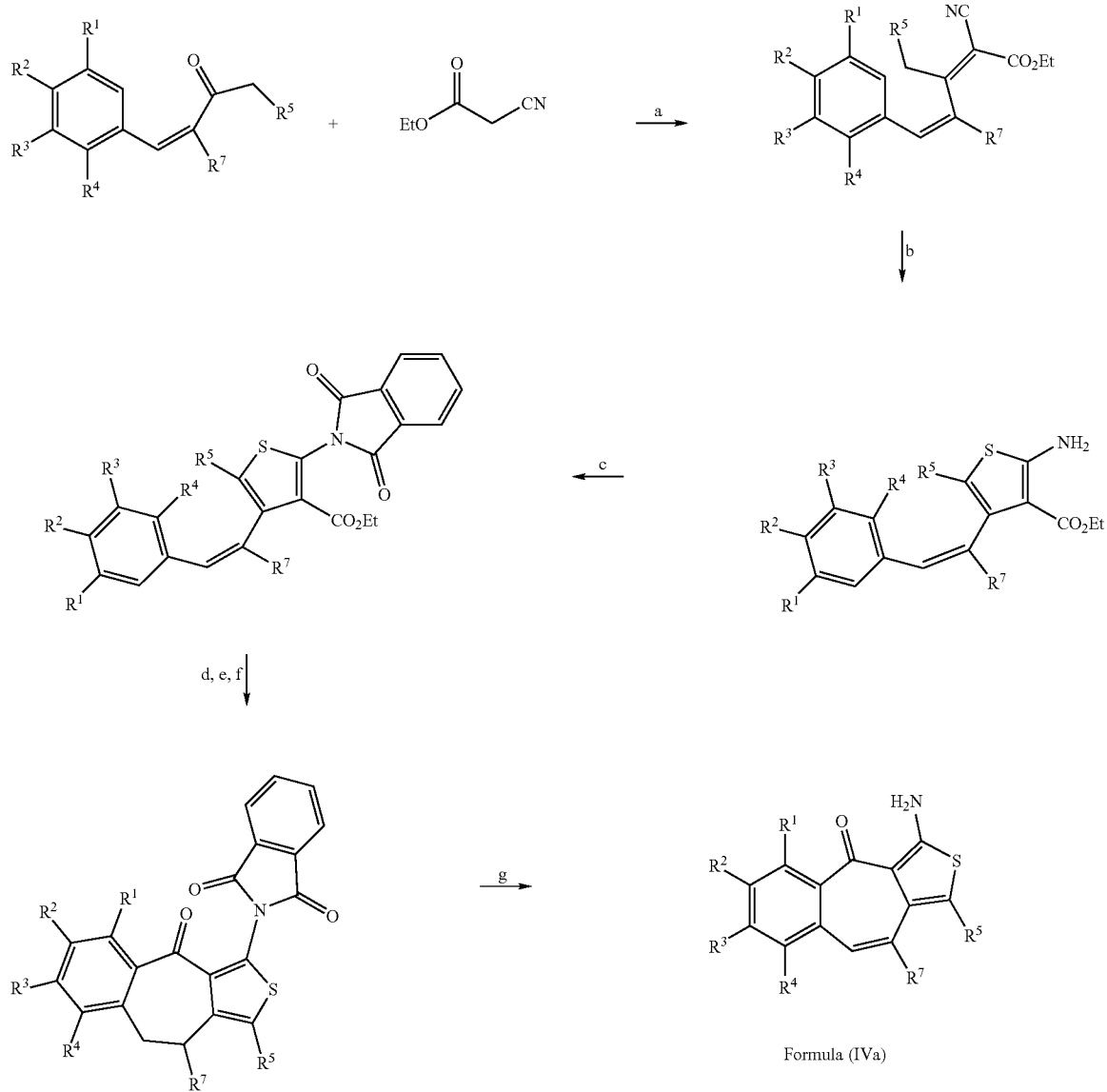

a. $CH_3CO_2^-NH_4^+$, $CH_3CO_2H$, benzene; b. morpholine, $S_8$, ethanol; c. phthalic anhydride, acetic acid; d. NaOH; e. $SOCl_2$; f. $AlCl_3$, $CH_2Cl_2$; g. $NH_2NH_2 \cdot H_2O$.

Knoevenagel condensation of ethyl cyanoacetate with a suitably substituted 4-aryl-3-buten-2-one gives the requisite 3-alkyl-5-aryl-2-cyano-pentadienoic acid esters that are converted to the corresponding 2-aminothiophene-3-carboxylate esters under the conditions of the Gewald reaction (Scheme IV). Protection of the amine, followed by base catalyzed hydrolysis of the ester, affords a late stage intermediate that is converted to the desired 3-amino-2-thia-benzo[f]azulen-4-ones of Formula (IVa) as that formula is specified in Scheme IV above by the methods described previously.

The preparation of compounds of Formulae (II), (III), or (IV) as those formulae are specified above containing a fourth fused ring arising from the elements $R^5$ and $R^7$ of these respective structures are preferentially synthesized in a manner similar to the methods described above, utilizing the requisite 2-substituted cycloalkanones or 2-(substituted)-heterocyclic ketones as a starting material. The requisite 2-aralkyl-cycloalkanones and 2-aralkyl-heterocyclic ketones are most expediently prepared by reaction of the enolate or enamine of the corresponding cycloalkanone or heterocyclic ketone with a suitable electrophile, such as the desired aralkyl chloride, bromide, mesylate, or tosylate for compounds of Formulae (II) and (III), or with an electrophile such as an aldehyde for compounds of Formula (IV) (Scheme V).

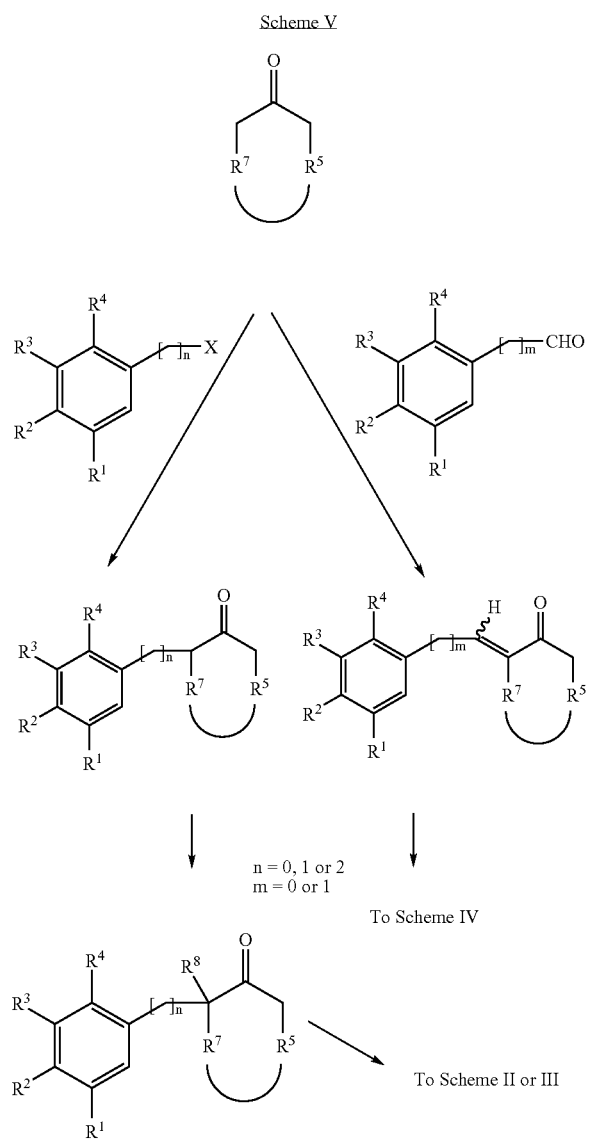

Scheme V n = 0, 1 or 2
m = 0 or 1

To Scheme IV

To Scheme II or III

Alternatively, the requisite 2-(substituted)-cycloalkanones or 2-(substituted)-heterocyclic ketones, in particular, the requisite 2-(aryl)-cycloalkanones or 2-(aryl)-heterocyclic ketones, are prepared by de novo synthesis of the requisite ketone-containing ring with the 2-substituent in place, utilizing methods known in the literature. In those instances where a second substituent is desired ($R^8 \neq$hydrogen), such compounds, particularly those of Formula (VIII) as that formula is specified above, are prepared either by a second regioselective alkylation of the 2-(substituted)-cycloalkanones or 2-(substituted)-heterocyclic ketones, using methods known to those skilled in the art, or by a de novo synthesis of the ketone-containing ring with both substituents in place. Conversion to the compounds of this invention utilizes the methods depicted in Schemes II, III, or IV.

As discussed above, compounds disclosed herein are useful to treat a variety of diseases and disorders.

Preferred therapies of the invention include treatment of pain, including pain management generally, and particularly treatment or management of chronic pain, especially neuropathic pain. Neuropathic pain has been recognized as pain resulting from some type of pathological damage to or condition relating to the nervous system. Various types of neuropathic pain may be treated in accordance with the invention, e.g., diabetic neuropathy and post herpetic neuralgia. Additional pathological conditions that can give rise to neuropathic pain that may be treated in accordance with the invention include trigeminal neuralgia, AIDS associated neuropathies due to HIV infection and/or treatment, pain associated with cancer treatment, whip-lash pain, phantom limb pain, traumatic injury pain, complex regional pain syndrome, and pain due to peripheral vascular disease. Methods of the invention also will be useful for management and treatment of post surgical pain.

Preferred therapies of the invention also include treatment and prophylaxis of hypoxia and/or ischemia induced injuries, e.g., stroke, infarction, heart attack, and the like. Typical subjects for such treatments include, e.g., heart attack, stroke, brain or spinal injury patients, patients undergoing major surgery such as heart surgery where brain ischemia is a potential complication, and the like.

Particular methods of the invention include administration of one or more fused thiophene compounds to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure can include intraoperative embolization and the danger of hypertension in the brain following increased cerebral blood flow, which can result in aneurysm or hemorrhage. Thus, an effective amount of one of more compounds of the invention could be administered pre-operatively or pert-operatively to reduce such risks associated with carotid endarterectomy, or other post-surgical neurological deficits.

The invention further includes methods for prophylaxis against neurological deficits resulting from, e.g., coronary artery bypass surgery and aortic valve replacement surgery, or other procedure involving extra-corporeal circulation. Those methods will suitably comprise administering to a patient undergoing surgical procedures an effective amount of one or more compounds of the invention, typically either pre-operatively or pert-operatively.

The invention also includes treatment of neurodegenerative disorders and diseases. Typical subjects will include mammals, particularly humans, afflicted with neurodegenerative diseases such as Parkinson's disease, Huntington's disease, Amyotrophic Lateral Sclerosis, Alzbeimer's disease, Down's Syndrome and Korsakoffs disease.

The invention also includes treatment of convulsant disorders, including treatment of a subject suffering from or susceptible to epilepsy.

Further preferred therapies include treatment or cardiac disorders and diseases, including treatment of adenosine-sensitive cardiac arrhythmias; cardioprotection, including both short term, e.g., prior to percutaneous angioplasty (PTDA), angioplasty, and cardiac surgeries, and long term, e.g., prophylaxis against myocardial infarction, especially in high risk patients, reduction of infarct damage, especially in high risk patients, and treatment of congestive heart failure.

Further provided are antilipid treatment methods including reduction of free fatty acids, triglycerides, glucose; adjunct therapy in diabetes, including, insulin dependent and non-insulin dependent diabetes mellitus, stimulation of insulin secretion from the pancreas, and increase in tissue sensitivity to insulin.

The invention also includes methods for treatment of gastrointestinal disorders such as diarrhea, irritable bowel disease, irritable bowel syndrome, irritable bladder, and incontinence such as urge incontinence.

Also provided are methods for treatment of elevated intraocular pressure in a subject, and particularly treatment of prophylaxis of glaucoma.

The invention also provides treatment of a subject suffering from a sleep disorder, including sleep apnea.

The invention further provides treatment of inflammation, including acute and chronic inflammatory condictions, e.g arthritic conditions, ulcerative colitis, and the like.

The treatment methods of the invention also will be useful for treatment of mammals other than humans, including for veterinary applications such as to treat horses and livestock, e.g., cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum cellular interstitial fluid, saliva, feces and urine) and cell and tissue samples of the above subjects will be suitable for use. Gentically modified cells and tissues, including modified cells and tissue of the above discussed subjects, also will be suitable for use.

A fused thiophene compound of the invention, including a compound of any of Formulae (I) through (IX), may be administered to a subject as the sole therapeutic agent in a particular therapeutic regime. Alternatively, one or more compounds of the invention may be administered as a "cocktail" formulation with other therapeutics, i.e., coordinated administration of one or more fused thiophene compounds of the invention together with one or more other active therapeutics, particularly a coordinated administration with adenosine or an adenosine derivative.

Preferred formulations of the present invention for medical use comprise one or more compounds of the invention together with an acceptable carrier thereof and optionally other therapeutically active ingredients. The carrier should be pharmaceutically acceptable in the sense of being compatible with the other ingredients of the formulation and not deleterious to the recipient thereof.

The present invention, therefore, further provides a pharmaceutical formulation comprising one or more compounds of the above formulae together with a pharmaceutically acceptable carrier thereof.

The formulations include, but are not limited to, those suitable for oral, rectal, topical, intrathecal or parenteral (including subcutaneous, intramuscular and intravenous) administration. Preferred are those suitable for oral or parenteral administration. The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound which is preferably isotonic with the blood of the recipient. Thus, such formulations may conveniently contain distilled water, 5% dextrose in distilled water or saline. Useful formulations also comprise concentrated solutions or solids containing the fused thiophene compound which upon dilution with an appropriate solvent give a solution suitable for parental administration above.

Formulations for parenteral administration or other administration route also may be admixed in an oil carrier, such as soybean oil.

Topical formulations include ointments, creams, gels and lotions which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

See, in general, Remington's Pharmaceutical Sciences (Mack Publishing Co., Aston, Pa.), for a discussion of suitable administration formulations.

Preferred pharmaceutical compositions or kits of the invention will comprise one or more fused thiophene compounds of the invention packaged together with instructions (written) for therapeutic use of the one or more compounds for a disease or disorder as disclosed herein, e.g., written instructions for therapeutic use of the one or more fused thiophene compounds for pain management particularly treatment or prophylaxis of chronic pain including neuropathic pain; treatment of neurological injuries; treatment of neurodegenerative disease or convulsant disease or disorder; treatment of cardiac disorders or diseases; treatment of gastrointestinal disorders, treatment of elevated intraocular pressure such as that associated with glaucoma; treatment of diabetes; and/or treatment of a sleep disorder.

Compounds of the invention are suitably administered to a subject in protonated and water-soluble form, e.g., as a pharmacuetically acceptable salt of an organic or inorganic acid, e.g., hydrochloride, sulfate, hemi-sulfate, phosphate, nitrate, acetate, oxalate, citrate, maleate, mesylate, etc., or as a salt of a suitable base or anion such as amines, e.g., ammonium compounds such as tetramethylammonium, and other organic amines such as trimethylamine and triethylamine, and alkali or alkaline earth metal salts such as sodium, potassium, calcium, etc.

Compounds of the invention can be assessed for specific activity in a variety of protocols. As discussed above, a preferred protocol is by measurement of cAMP enhancement in CHO cells ("cAMP enhancement assay"), as exemplified in Example 34, which follows.

The amount of compound of the present invention required to be effective as an allosteric modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 pg/kg to about 100 mg/kg body weight per day, preferably in the range of about 1 mg/kg to about 30 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 2200 mg per day, and a typical dose would be about 150 mg per day. If discrete multiple doses are indicated, treatment might typically be 5 mg of a compound of the present invention given 3 times per day.

All documents mentioned herein are incorporated herein by reference.

The following non-limiting examples are illustrative of the invention.

EXAMPLE 1

Part A: 2-Cyano-3-phenyl-but-2-enoic acid ethyl ester

A mixture of acetophenone (50 mmol), ethyl cyanoacetate (50 mmol), acetic; acid (1.14 mL), ammonium acetate (400 mg), and benzene (50 mL) was heated to reflux in a Dean-Stark apparatus. After approximately 10 hours, additional ethyl cyanoacetate (50 mmol), acetic acid (1.14 mL), and ammonium acetate (400 mL) are added. After an additional 10 hours, the reaction was cooled to room temperature, diluted with ethyl acetate (30 mL), washed with water (240 mL), brine (40 mL), and dried ($Na_2SO_4$). After filtering, the extract was concentrated in vacuo and the desired product, as a mixture of E and Z-isomers, was isolated by column chromatography on silica gel, eluting with 5% ethyl acetate in petroleum ether, affording an oil that solidified on standing at room temperature.

Yield: 79%. Lit. Yield: 59%. $^1$H-NMR ($CDCl_3$): δ 1.07 (t, 3H, J=7.1 Hz), 1.34 (t, 3H, J=7.2 Hz), 2.50 (s, 3H), 2.65 (s, 3H), 4.03 (q, 2H, J=7.2 Hz), 4.28 (q, 2H, J=7.1 Hz), 7.30 (m, 10H). (*Eur. J. Med. Chem. Chim. Ther.* 15: 563 (1980)).

Part B: 2-Amino-4-phenylthiophene-3-carboxylic acid ethyl ester

The mixture of E and Z-isomers of 2-cyano-3-phenyl-but-2-enoic acid ethyl ester (39.5 mmol, Example 1, Part A), morpholine (39.5 mmol), and sulfur (39.5 mmol) in ethanol (100 mL) was heated to reflux for 1.5-3.0 hours. After cooling to room temperature, the mixture was concentrated in vacuo and the residue dissolved in ethyl acetate (30 mL). After washing with water (15 mL) and brine (15 mL), the organic layers was dried ($Na_2SO_4$), filtered, and concentrated. The residue was chromatographed on a column of silica gel, eluting with 10% ethyl acetate in petroleum ether, to afford the desired product as a yellow oil. Yield: 79%.

$^1$H-NMR ($CDCl_3$): δ 0.94 (t, 3H, J=7.2 Hz), 4.04 (q, 2H, J=7.2 Hz), 6.07 (s, 1H), 6.08 (bs, 2H), 7.30 (m, 8H). (*Eur. J. Med. Chem. Chim. Ther.* 15: 563 (1980)).

Part C: 2-(1,3-Dioxo-1,3-dihydroisoindol-2-yl)-4-phenyl-thiophene-3-carboxylic acid ethyl ester A mixture of 2-amino-4-phenylthiophene-3-carboxylic acid ethyl ester (2 mmol, Example 1, Part B) and phthalic anhydride (2.2 mmol) in glacial acetic acid (20 mL) was heated at reflux overnight. After cooling to room temperature, the acetic acid was removed in vacuo and the residue triturated with petroleum ether. The crude product was collected by filtration, suspended in acetyl chloride (5 mL), and heated to reflux for one hour. After removing the solvent in vacuo the residue was dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization from petroleum ether afforded the desired product as a yellow solid in 70% yield.

MP: 163-164° C.; $^1$H-NMR (DMSO-$d_6$): δ 0.89 (t, 3H, J=7.0 Hz), 3.99 (q, 2H, J=7.0 Hz), 7.01 (s, 1H), 7.32 (m, 5H), 7.73 (m, 4H).

Part D: 2-(1,3-Dioxo-1,3-dihydroisoindol-2-yl)-4-phenyl-thiophene-3-carboxylic acid To a solution of NaOH (1.4 mmol) in a 1:1 mixture of methanol:$H_2O$ (6 mL) was added 2-(1,3-dioxo-1,3-dihydroisoindol-2-yl)-4-phenyl-thiophene-3-carboxylic acid ethyl ester (0.7 mmol, Example 1, Part C). The mixture was heated to reflux for 90 min, then diluted with water (12 mL), chilled in an ice bath, and acidified with concentrated HCl. The product that precipitated was collected by filtration, washed with water, and dried, affording the desired compound as a white solid in 92% yield.

MP: 198-199° C.; $^1$H-NMR (DMSO-$d_6$): δ 6.95 (s, 1H), 7.33 (m, 5H), 7.71 (m, 3H), 7.92 (m, 1H), 13.20 (bs, 1H).

Part E: 2-(8-Oxo-8H-2-thia-cyclopenta[a]inden-1-yl)-isoindole-1,3-dione

A suspension of 2-(1,3-dioxo-1,3-dihydroisoindol-2-yl)-4-phenyl-thiophene-3-carboxylic acid (1.15 mmol, Example 1, Part D) in thionyl chloride (3 mL) was heated to reflux for 30 min, providing a homogeneous solution. The mixture was concentrated to afford the crude acid chloride, then co-evaporated with four successive aliquots of benzene to remove the last traces of thionyl chloride, providing the acid chloride as a yellow-brown solid.

The crude acid chloride, dissolved in anhydrous methylene chloride (3 mL), was added to a suspension of anhydrous aluminum chloride (4.60 mmol) in anhydrous methylene chloride (5 mL). The resulting red-brown mixture was heated to reflux for three hours, cooled to room temperature, and poured onto a mixture of 1 M HCl (20 mL) and ice. The organic layer was collected and the aqueous layer extracted with additional methylene chloride (2×10 mL). The combined organic layers were washed with water (10 mL), brine (10 mL), dried (Na$_2$SO$_4$), filtered, and concentrated. The residue was applied to a short column of silica gel, eluting with ethyl acetate, to afford the desired product as a white solid. Yield: 50%.

MP: 197-199° C.; $^1$H-NMR (DMSO-d$_6$): δ 7.37 (t, 1H, J=7.5 Hz), 7.61 (d, 1H, J=7.25 Hz), 7.64 (t, 1H, J=7.5 Hz), 7.74 (d, 1H, J=7.2 Hz), 7.78 (s, 1H), 7.98 (m, 4H).

Part F: 1-Amino-2-thia-cyclopenta[a]inden-8-one. [Formula (I): R$^1$=R$^2$=R$^3$=R$^4$=R$^5$=R$^6$=H; R$^9$+R$^{10}$=O]

To a suspension of 2-(8-oxo-8H-2-thia-cyclopenta[a]inden-1-yl)-isoindole-1,3-dione (0.45 mmol, Example 1, Part E) in absolute ethanol (5 mL) was added hydrazine hydrate (0.5 mmol). The mixture was heated to reflux for one hour, cooled to room temperature, concentrated in vacuo, and the residue dissolved in methylene chloride. The solution was chilled to 5° C. for one hour, during which time the phthaloyl hydrazide precipitated. The precipitate was removed by filtration, the filtrate concentrated in vacuo, and the residue purified by column chromatography on silica gel, eluting with a 4:1 mixture of petroleum ether:ethyl acetate. Fractions containing the product were collected, evaporated, and the product, recrystallized from petroleum ether, was isolated as a yellow solid. Yield: 80%.

MP: 136° C.; $^1$H-NMR (CDCl$_3$): δ 6.61 (s, 1H), 7.28 (t, 1H, J=7.3 Hz), 7.48 (m, 3H), 7.71 (bs, 2H); IR (KBr): 3301, 3204, 1668, 1536 cm$^{-1}$.

EXAMPLES 2 AND 3

Part A: 2-Cyano-3-(3-methylphenyl)-but-2-enoic acid ethyl ester

A mixture of 3'-methylacetophenone (50 mmol), ethyl cyanoacetate (50 mmol), 25 acetic acid (1.14 mL) ammonium acetate (400 mg), and benzene (50 mL) was heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction was cooled to room temperature, diluted with ethyl acetate (30 mL), washed with water (240 mL), brine (40 mL), and 30 dried (Na$_2$SO$_4$). After filtering, the extract was concentrated in vacuo and the desired product, as a mixture of E and Z-isomers, was isolated by column chromatography on silica gel, eluting with 5% ethyl acetate in petroleum ether. The purified oil solidified on standing at room temperature.

Yield: 75%. $^1$H-NMR (CDCl$_3$): δ 1.07 (t, 3H, J=7.15 Hz), 1.33 (t, 3H, J=7. Hz), 5 2.40 (s, 3H), 2.42 (s, 3H), 2.56 (s, 3H), 2.70 (s, 3H), 4.07 (q, 2H, J=7.15 Hz), 4.20 (q, 2H, J=7.15 Hz), 7.20 (m, 8H). (*Tetrahed. Lett.* 41: 7563 (2000)).

Part B: 2-Amino-4-(3-methylphenyl)-thiophene-3-carboxylic acid ethyl ester

The mixture of E and Z-isomers of 2-cyano-3-(3-methylphenyl)-but-2-enoic acid ethyl ester (39.5 mmol, Example 2 & 3, Part A), morpholine (39.5 mmol), and sulfur (39.5 mmol) in ethanol (100 mL) was heated to reflux for 1.5-3.0 hours. After cooling to room temperature, the mixture was concentrated in vacuo and the residue dissolved in ethyl acetate (30 mL). After washing with water (15 mL) and brine (15 mL), the organic layers was dried (Na$_2$SO$_4$), filtered, and concentrated. The residue was chromatographed on a column of silica gel, eluting with 10% ethyl acetate in petroleum ether, to afford the desired product as a yellow oil.

Yield: 70%. $^1$H-NMR (CDCl$_3$): δ 0.94 (t, 3H, J=7.2 Hz), 2.35 (s, 3H), 4.02 (q, 2H, J=7.2 Hz), 6.05 (s, 1H), 6.07 (bs, 2H), 7.16 (m, 4H).

Part C: 2-(1,3-Dioxo-1,3-dihydroisoindol-2-yl)-4-(3-methylphenyl)-thiophene-3-carboxylic acid ethyl ester A mixture of 2-amino-4-(3-methylphenyl)-thiophene-3-carboxylic acid ethyl ester (2 mmol, Example 2 & 3, Part B) and phthalic anhydride (2.2 mmol) in glacial acetic acid (20 mL) was heated at reflux overnight. After cooling to room temperature, the acetic acid was removed in vacuo and the residue triturated with petroleum ether. The crude product was collected by filtration, suspended in acetyl chloride (5 mL), and heated to reflux for one hour. After removing the solvent in vacuo, the residue was dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization from petroleum ether afforded the desired product as a yellow solid in 63% yield.

MP: 175-176° C.; $^1$H-NMR (DMSO-d$_6$): δ 0.75 (t, 3H, J=7.2 Hz), 2.33 (s, 3H), 3.92 (q, 2H, J=7.2 Hz), 7.23 (m, 4H), 7.66 (s, 1H), 7.98 (m, 4H).

Part D: 2-(1,3-Dioxo-1,3-dihydroisoindol-2-yl)-4-(3-methylphenyl)-thiophene-3-carboxylic acid To a solution of NaOH (1.4 mmol) in a 1:1 mixture of methanol:H$_2$O (6 mL) was added 2-(1,3-dioxo-1,3-dihydroisoindol-2-yl)-4-(3-methylphenyl)-thiophene-3-carboxylic acid ethyl ester (0.7 mmol, Example 2 & 3, Part C). The mixture was heated to reflux for 90 min, then diluted with water (12 mL), chilled in an ice bath, and acidified with concentrated HCl. The product that precipitated was collected by filtration, washed with water, and dried, affording the desired compound as a white solid in 94% yield.

MP: 195° C.; $^1$H-NMR (DMSO-d$_6$): δ 2.31 (s, 3H), 6.92 (s, 1H), 7.20 (m, 4H), 7.68 (m, 3H), 7.91 (m, 1H), 13.18 (bs, 1H).

Part E: 2-(5-Methyl-8-oxo-8H-2-thia-cyclopenta[a]inden-1-yl)-isoindole-1,3-dione and 2-(7-Methyl-8-oxo-8H-2-thia-cyclopenta[a]inden-1-yl)-isoindole-1,3-dione A suspension of 2-(1,3-dioxo-1,3-dihydroisoindol-2-yl)-4-(3-methylphenyl)-thiophene-3-carboxylic acid (1.15 mmol, Example 2 & 3, Part D) in thionyl chloride (3 mL) was heated to reflux for 30 min, providing a homogeneous solution. The mixture was concentrated to afford the crude acid chloride, then co-evaporated with four successive aliquots of benzene to remove the last traces of thionyl chloride, providing the acid chloride as a yellow-brown solid.

The crude acid chloride, dissolved in anhydrous methylene chloride (3 mL), was added to a suspension of anhydrous aluminum chloride (4.60 mmol) in anhydrous methylene chloride (5 mL). The resulting red-brown mixture was heated to reflux for three hours, cooled to room temperature, and poured onto a mixture of 1 M HCl (20 mL) and ice. The organic layer was collected and the aqueous layer extracted with additional methylene chloride (2×10 mL). The combined organic layers were washed with water (10 mL), brine (10 mL), dried (Na2SO4), filtered, and concentrated. The residue was applied to a short column of silica gel, eluting with ethyl acetate, to afford a mixture of the two isomeric products as a white solid, which was used without further purification. Yield: 80%.

EXAMPLE 2

Part F: 1-Amino-7-methyl-2-thia-cyclopenta[a]inden-8-one. [Formula (I): $R^1=CH_3$; $R^2=R^3=R^4=R^5=R^6=H$; $R^9+R^{10}=O$]; and

EXAMPLE 3

Part F: 1-Amino-5-methyl-2-thia-cyclopenta[a]inden-8-one [Formula (I): $R^3=CH_3$; $R^1=R^2=R^4=R^5=R^6=H$; $R^9+R^{10}=O$]

To a mixture of 2-(5-methyl-8-oxo-8H-2-thia-cyclopenta [a]inden-1-yl)-isoindole-1,3-dione and 2-(7-methyl-8-oxo-8H-2-thia-cyclopenta[a]inden-1-yl)-isoindole-1,3-dione (0.45 mmol, Example & 3, Part E) in absolute ethanol (5 mL) was added hydrazine hydrate (0.5 mmol). The suspension was heated to reflux for one hour, cooled to room temperature, concentrated in vacuo, and the residue dissolved in methylene chloride. The solution was chilled to 5° C. for one hour, during which time the phthaloyl hydrazide precipitated. The precipitate was removed by filtration, the filtrate concentrated in vacuo, and the residue purified by column chromatography on silica gel, eluting with a 4:1 mixture of petroleum ether: ethyl acetate. Fractions containing the individual products were pooled, evaporated, and each product was isolated after recrystallization from petroleum ether.

1-Amino-7-methyl-2-thia-cyclopenta[a]inden-8-one

Yield: 61%. Yellow solid. MP: 196-198° C.; $^1$H-NMR (CDCl$_3$): δ 2.63 (s, 3H), 5.42 (bs, 2H), 6.25 (s, 1H), 7.00 (d, 1H, J=7.4 Hz), 7.28 (m, 2H); IR (KBr): 3273, 3195, 1659, 1543 cm$^{-1}$.

1-Amino-5-methyl-2-thia-cyclopenta[a]inden-8-one

Yield: 20%. Yellow solid. MP: 157-159° C.; $^1$H-NMR (CDCl$_3$): δ 2.40 (s, 3H), 5.46 (bs, 2H), 6.26 (s, 1H), 7.07 (d, 1H, J=7.76 Hz), 7.22 (s, 1H), 7.53 (d, 1H, J=7.76 Hz); IR (KBr): 3262, 3185, 1659, 1542 cm$^{-1}$.

EXAMPLE 4 AND 5

Part A: 3-(3-Chlorophenyl)-2-cyano-but-2-enoic acid ethyl ester

A mixture of 3'-chloroacetophenone (50 mmol), ethyl cyanoacetate (50 mmol), acetic acid (1.14 mL) ammonium acetate (400 mg), and benzene (50 mL) was heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction was cooled to room temperature, diluted with ethyl acetate (30 mL), washed with water (240 mL), brine (40 mL), and dried (Na$_2$SO$_4$). After filtering, the extract was concentrated in vacuo and the desired product, as a 1:1 mixture of E and Z-isomers, was isolated by column chromatography on silica gel, eluting with 5% ethyl acetate in petroleum ether. The purified oil solidified on standing at room temperature Yield: 60%.

$^1$H-NMR (CDCl$_3$): δ 1.16 (t, 3H, J=7.2 Hz), 1.38 (t, 3H, J=7.15 Hz), 2.53 1 (s, 3H), 2.63 (s, 3H), 4.10 (q, 2H, J=7.15 Hz), 4.33 (q, 2H, J=7.2 Hz), 7.31 (m, 8H).

Part B: 2-Amino-4-(3-chlorophenyl)-thiophene-4-carboxylic acid ethyl ester

The mixture of E and Z-isomers of 2-cyano-3-(3-chlorophenyl)-but-2-enoic acid ethyl ester (39.5 mmol, Example 4 & 5, Part A) morpholine (39.5 mmol), and sulfur (39.5 mmol) in ethanol (100 mL) was heated to reflux for 1.5-3.0 hours. After cooling to room temperature, the mixture was concentrated in vacuo and the residue dissolved in ethyl acetate (30 mL). After washing with water (15 mL) and brine (15 mL), the organic layers was dried (Na$_2$SO$_4$), filtered, and concentrated. The residue was chromatographed on a column of silica gel, eluting with 10% ethyl acetate in petroleum ether, to afford the desired product as a yellow oil that solidifies on standing. Yield: 86%.

$^1$H-NMR (CDCl$_3$): δ 1.01 (t, 3H, J=7.2 Hz), 4.07 (q, 2H, J=7.2 Hz), 6.11 (s, 1H), 6.16 (bs, 2H), 7.27 (m, 4H).

Part C: 4-(3-Chlorophenyl)-2-(1,3-dioxo-1,3-dihydroisoindol-2-yl)-thiophene-3-carboxylic acid ethyl ester A mixture of 2-amino-4-(3-chlorophenyl)-thiophene-3-carboxylic acid ethyl ester (2 mmol, Example 4 & 5, Part B) and phthalic anhydride (2.2 mmol) in glacial acetic acid; (20 mL) was heated at reflux overnight. After cooling to room temperature, the acetic acid was removed in vacuo and the residue triturated with petroleum ether. The crude product was collected by filtration, suspended in acetyl chloride (5 mL), and heated to reflux for one hour. After removing the solvent in vacuo, the residue was dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization from petroleum ether afforded the desired product as a yellow solid in 80% yield.

MP: 169° C.; $^1$H-NMR (DMSO-d$_6$): δ 0.76 (t, 3H, J=7.15 Hz), 3.92 (q, 2H, J=7.15 Hz), 7.31 (m, 1H), 7.43 (m, 3H), 7.80 (s, 1H), 8.00 (m, 4H).

Part D: 4-(3-Chlorophenyl)-2-(1,3-Dioxo-1,3-dihydroisoindol-2-yl)-thiophene-3-carboxylic acid To a solution of NaOH (1.4 mmol) in a 1:1 mixture of methanol:H$_2$O (6 mL) was added 4-(3-chlorophenyl)-2-(1,3-dioxo-1,3-dihydroisoindol-2-yl)-thiophene-3-carboxylic acid ethyl ester (0.7 mmol, Example 4 & 5, Part C). The mixture was heated to reflux for 90 min, then diluted with water (12 mL), chilled in an ice bath, and acidified with concentrated HCl. The product that precipitated was collected by filtration, washed with water, and dried, affording the desired compound as a white solid in 90% yield.

MP: 203-204° C.; $^1$H-NMR (DMSO-d$_6$): δ 7.04 (s, 1H), 7.30 (m, 1H), 7.34 (m, 3H), 7.68 (m, 3H), 7.91 (m, 1H), 13.24 (bs, 1H).

Part E: 2-(5-Chloro-8-oxo-8H-2-thia-cyclopenta[a] inden-1-yl)-isoindole-1,3-dione and 2-(7-Chloro 8-oxo-8H-2-thia-cyclopenta[a]inden-1-yl)-isoindole-1,3-dione A suspension of 4-(3-chlorophenyl)-2-(1,3-dioxo-1,3-dihydroisoindol-2-yl)-thiophene-3-carboxylic acid (1.15 mmol, Example 4 & 5, Part D) in thionyl chloride (3 mL) was heated to reflux for 30 min, providing a homogeneous solution. The mixture was concentrated to afford the crude acid chloride, then co-evaporated with four successive aliquots of benzene to remove the last traces of thionyl chloride, providing the acid chloride as a yellow-brown solid.

The crude acid chloride, dissolved in anhydrous methylene chloride (3 mL), was added to a suspension of anhydrous aluminum chloride (4.60 mmol) in anhydrous methylene chloride (5 mL). The resulting red-brown mixture was heated to reflux for three hours, cooled to room temperature, and poured onto a mixture of 1 M HCl (20 mL) and ice. The organic layer was collected and the aqueous layer extracted with additional methylene chloride (2×10 mL). The combined organic layers were washed with water (10 mL), brine (10 mL), dried ($Na_2SO_4$), filtered, and concentrated. The residue was applied to a short column of silica gel, eluting with ethyl acetate, to afford a mixture of the two isomeric products as a white solid, which was used without further purification. Yield: 35%.

EXAMPLE 4

Part F: 1-Amino-7-chloro-2-thia-cyclopenta[a]inden-8-one. [Formula (I): $R^1$=Cl; $R^2$=$R^3$=$R^4$=$R^5$=$R^6$=H; $R^9$+$R^{10}$=O]; and

EXAMPLE 5

Part F: 1-Amino-5-chloro-2-thia-cyclopenta[a]inden-8-one. [Formula (I): $R^3$=Cl; $R^1$=$R^2$=$R^4$=$R^5$=$R^6$=H; $R^9$+$R^{10}$=O]

To a mixture of 2-(5-chloro-8-oxo-8H-2-thia-cyclopenta[a]inden-1-yl)-isoindole-1,3-dione and 2-(7-chloro-8-oxo-8H-2-thia-cyclopenta[a]inden-1-yl)-isoindole-1,3-dione (0.45 mmol, Example 4 & 5, Part E) in absolute ethanol (5 mL) was added hydrazine hydrate (0.5 mmol). The suspension was heated to reflux for one hour, cooled to room temperature, concentrated in vacuo, and the residue dissolved in methylene chloride. The solution was chilled to 5° C. for one hour, during which time the phthaloyl hydrazide precipitated. The precipitate was removed by filtration, the filtrate concentrated in vacuo, and the residue purified by column chromatography on silica gel, eluting with a 4:1 mixture of petroleum ether:ethyl acetate. Fractions containing the individual products were pooled, evaporated, and each product was isolated after recrystallization from petroleum ether.

1-Amino-7-chloro-2-thia-cyclopenta[a]inden-8-one

Yield: 12%. Yellow solid. MP: 183-185° C.; $^1$H-NMR ($CDCl_3$): δ 5.54 (bs, 2H), 6.30 (s, 1H), 7.20 (d, 1H, J=7.8 Hz), 7.30 (m, 2H); IR (KBr): 3254, 3175, 1659, 1538 $cm^{-1}$.

1-Amino-5-chloro-2-thia-cyclopenta[a]inden-8-one

Yield: 58%. Yellow solid. MP: 201-202° C., $^1$H-NMR ($CDCl_3$): δ 5.56 (bs, 2H), 6.32 (s, 1H), 7.23 (d, 1H, J=8.00 Hz), 7.38 (s, 1H), 7.56 (d, 1H, J=8.00 Hz); IR (KBr): 3259, 3180, 1663, 1536 $cm^{-1}$.

EXAMPLES 6 AND 7

Part A: 2-Cyano-3-(3,4-dichlorophenyl)-but-2-enoic acid ethyl ester

A mixture of 3',4'-dichloroacetophenone (50 mmol), ethyl cyanoacetate (50 mmol), acetic acid (1.14 mL) ammonium acetate (400 mg), and benzene (50 mL) was heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction was cooled to room temperature, diluted with ethyl acetate (30 mL), washed with water (240 mL), brine (40 mL), and dried ($Na_2SO_4$). After filtering, the extract was concentrated in vacuo and the desired product, as a 1:1 mixture of E and Z-isomers, was isolated by column chromatography on silica gel, eluting with 5% ethyl acetate in petroleum ether. The purified oil solidified on standing at room temperature. Yield: 60%.

$^1$H-NMR ($CDCl_3$): δ 1.20 (t, 3H, J=7.2 Hz), 1.38 (t, 3H, J=7. Hz), 2.52 (s, 3H), 2.66 (s, 3H), 4.13 (q, 2H, J=7.1 Hz), 4.33 (q, 2H, J=7.2 Hz), 7.31 (m, 6H).

Part B: 2-Amino-4-(3,4-dichlorophenyl)-thiophene-3-carboxylic acid ethyl ester

The mixture of E and Z-isomers of 2-cyano-3-(3-methylphenyl)-but-2-enoic acid ethyl ester (39.5 mmol, Example 6 & 7, Part A), morpholine (39.5 mmol), and sulfur (39.5 mmol) in ethanol (100 mL) was heated to reflux for 1.5-3.0 hours. After cooling to room temperature, the mixture was concentrated in vacuo and the residue dissolved in ethyl acetate (30 mL). After washing with water (15 mL) and brine (15 mL), the organic layers was dried ($Na_2SO_4$), filtered, and concentrated. The residue was chromatographed on a column of silica gel, eluting with 10% ethyl acetate in petroleum ether, to afford the desired product as a yellow oil that solidifies on standing. Yield: 71%.

$^1$H-NMR ($CDCl_3$): δ 1.02 (t, 3H, J=7.15 Hz), 4.06 (q, 2H, J=7.15 Hz), 6.07 (s, 1H), 6.15 (bs, 2H), 7.14 (dd, 1H, J=8 Hz, 2 Hz), 7.38 (d, 1H, J=8 Hz), 7.41 (s, 1H).

Part C: 4-(3,4-Dichlorophenyl)-2-(1,3-dioxo-1,3-dihydroisoindol-2-yl)-thiophene-3-carboxylic acid ethyl ester A mixture of 2-amino-4-(3,4-dichlorophenyl)-thiophene-3-carboxylic acid ethyl ester (2 mmol, Example 6 & 7, Part B) and phthalic anhydride (2.2 mmol) in glacial acetic acid (20 mL) was heated at reflux overnight. After cooling to room temperature, the acetic acid was removed in vacuo and the residue triturated with petroleum ether. The crude product was collected by filtration, suspended in acetyl chloride (5 mL), and heated to reflux for one hour. After removing the solvent in vacuo, the residue was dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization from petroleum ether afforded the desired product as a yellow solid in 74% yield.

MP: 155-156° C.; $^1$H-NMR (DMSO-$d_6$): δ 0.75 (t, 3H, J=7.15 Hz), 3.90 (q, 2H, J=7.0 Hz), 7.35 (dd, 1H, J=8.0 Hz, 2 Hz), 7.64 (d, 1H, J=8.0 Hz), 7.65 (s, 1H), 7.80 (s, 1H), 8.10 (m, 4H).

Part D: 4-(3,4-Dichlorophenyl)-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) was added 4-(3,4-dichlorophenyl)-2-(1,3-dioxo-1,3-dihydroisoindol-2-yl)-thiophene-3-carboxylic acid ethyl ester (0.7 mmol, Example 6 & 7, Part C). The mixture was heated to reflux for 90 min, then diluted with water (12 mL), chilled in an ice bath, and acidified with concentrated HCl. The product that precipitated was collected by filtration, washed with water, and dried, affording the desired compound as a white solid in 92% yield.

MP: 198-199° C.; $^1$H-NMR (DMSO-$d_6$): δ 7.15 (s, 1H), 7.40 (dd, 1H, J=8.0 Hz, 2.0 Hz), 7.66 (d, 1H, J=8.0 Hz), 7.68 (s, 1H), 7.88 (m, 3H), 7.96 (m, 1H), 13.25 (bs, 1H).

Part E: 2-(5,6-Dichloro-8-oxo-8H-2-thia-cyclopenta [a]inden-1-yl)-isoindole-1,3-dione and 2-(6,7-Dichloro-8-oxo-8H-2-thia-cyclopenta[a]inden-1-yl)-isoindole-1,3-dione A suspension of 4-(3,4-dichlorophenyl)-2-(1,3-dioxo-1,3-dihydroisoindol-2-yl)-thiophene-3-carboxylic acid (1.15 mmol, Example 6 & 7, Part D) in thionyl chloride (3 mL) was heated to reflux for 30 min, providing a homogeneous solution. The mixture was concentrated to afford the crude acid chloride, then co-evaporated with four successive aliquots of benzene to remove the last traces of thionyl chloride, providing the acid chloride as a yellow-brown solid.

The crude acid chloride, dissolved in anhydrous methylene chloride (3 mL), was added to a suspension of anhydrous aluminum chloride (4.60 mmol) in anhydrous methylene chloride (5 mL). The resulting red-brown mixture was heated to reflux for three hours, cooled to room temperature, and poured onto a mixture of 1 M HCl (20 mL) and ice. The organic layer was collected and the aqueous layer extracted with additional methylene chloride (2×10 mL). The combined organic layers were washed with water (10 mL), brine (10 mL), dried (Na$_2$SO$_4$), filtered, and concentrated. The residue was applied to a short column of silica gel, eluting with ethyl acetate, to afford a mixture of the two isomeric products as a white solid, which was used without further purification. Yield: 25%.

EXAMPLE 6

Part F: 1-Amino-6,7-chloro-2-thia-cyclopenta[a] inden-8-one. [Formula (I): $R^1$=$R^2$=Cl; $R^3$=$R^4$=$R^5$=$R^6$=H; $R^9$+$R^{10}$=O]; and

EXAMPLE 7

Part F: 1-Amino-5,6-chloro-2-thia-cyclopenta[a] inden-8-one. [Formula (I): $R^2$=$R^3$=Cl; $R^1$=$R^4$=$R^5$=$R^6$=H; $R^9$+$R^{10}$=O]

To a mixture of 2-(5,6-dichloro-8-oxo-8H-2-thia-cyclopenta[a]inden-1-yl)-isoindole-1,3-dione and 2-(6,7-dichloro-8-oxo-8H-2-thia-cyclopenta[a]inden-1-yl)-isoindole-1,3-dione (0.45 mmol, Example 6 & 7, Part E) in absolute ethanol (5 mL) was added hydrazine hydrate (0.5 mmol). The suspension was heated to reflux for one hour, cooled to room temperature, concentrated in vacuo, and the residue dissolved in methylene chloride. The solution was chilled to 5° C. for one hour, during which time the phthaloyl hydrazide precipitated. The precipitate was removed by filtration, the filtrate concentrated in vacuo, and the residue purified by column chromatography on silica gel, eluting with methylene chloride. Fractions containing the individual products were pooled, evaporated, and each product was isolated after recrystallization from petroleum ether.

1-Amino-6,7-dichloro-2-thia-cyclopenta[a]inden-8-one

Yield: 17%. Yellow solid. MP: 254-255° C.; $^1$H-NMR (DMSO-$d_6$): δ 6.75 (s, 1H), 7.55 (d, 1H, J=8.0 Hz), 7.70 (d, 1H, J=8.0 Hz), 7.92 (bs, 2H); IR (KBr): 3417, 3232, 1664, 1534 cm$^{-1}$.

1-Amino-5,6-dichloro-2-thia-cyclopenta[a inden-8-one

Yield: 43%. Yellow solid. MP: 272° C.; $^1$H-NMR (DMSO-$d_6$): 6.75 (s, 1H), 7.65 (s, 1H), 7.92 (s, 1H), 7.98 (bs, 2H); IR (KBr): 3463, 3332, 1688, 1558 cm$^{-1}$.

EXAMPLE 8

Part A: 3-(2-Chlorophenyl)-2-cyano-but-2-enoic acid ethyl ester

A mixture of 2'-chloroacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(2-chlorophenyl)-thiophene-3-carboxylic acid ethyl ester

The mixture of E and Z-isomers of 2-cyano-3-(2-chlorophenyl)-but-2-enoic acid ethyl ester (39.5 mmol, Example 8, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a column of silica gel, eluting with 10% ethyl acetate in petroleum ether, to afford the desired product.

Part C: 4-(2-Chlorophenyl)-2-(1,3-dioxo-1,3-dihydroisoindol-2-yl)-thiophene-3-carboxylic acid ethyl ester A mixture of 2-amino-4-(2-chlorophenyl)-thiophene-3-carboxylic acid ethyl ester (2 mmol, Example 8, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization from petroleum ether affords the desired product.

Part D: 4-(2-Chlorophenyl)-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-(2-chlorophenyl)-2-(1,3-dioxo-1,3-dihydroisoindol-2-yl)-thiophene-3-carboxylic acid ethyl ester (0.7 mmol, Example 8, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(4-Chloro-8-oxo-8H-2-thia-cyclopenta[a]inden-1-yl)-isoindole-1,3-dione A suspension of 2-(1,3-dioxo-1,3-dihydroisoindol-2-yl)-4-(2-chlorophenyl)-thiophene-3-carboxylic acid (1.15 mmol, Example 8, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride. The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 1-Amino-4-chloro-2-thia-cyclopenta[a]inden-8-one. [Formula (I): $R^4$=Cl; $R^1$=$R^2$=$R^3$=$R^5$=$R^6$=H; $R^9$+$R^{10}$=O]

To a suspension of 2-(4-chloro-8-oxo-8H-2-thia-cyclopenta[a]inden-1-yl)-isoindole-1,3-dione (0.45 mmol, Example 8, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 9

Part A: 3-(4-Chlorophenyl)-2-cyano-but-2-enoic acid ethyl ester

A mixture of 4'-chloroacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(4-chlorophenyl)-thiophene-3-carboxylic acid ethyl ester

The mixture of E and Z-isomers of 2-cyano-3-(4-chlorophenyl)-but-2-enoic acid ethyl ester (39.5 mmol, Example 9, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 4-(4-Chlorophenyl)-2-(1,3-dioxo-1,3-dihydroisoindol-2-yl)-thiophene-3-carboxylic acid ethyl ester A mixture of 2-amino-4-(4-chlorophenyl)thiophene-3-carboxylic acid ethyl ester (2 mmol, Example 9, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 4-(4-Chlorophenyl)-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-(4-chlorophenyl)-2-(1,3-dioxo-1,3-dihydroisoindol-2-yl)-thiophene-3-carboxylic acid ethyl ester (0.7 mmol, Example 9, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(6-Chloro-8-oxo-8H-2-thia-cyclopenta[a]inden-1-yl)-isoindole-1,3-dione A suspension of 4-(4-chlorophenyl)-2-(1,3-dioxo-1,3-dihydroisoindol-2-yl)-thiophene-3-carboxylic acid (1.15 mmol, Example 9, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-6-chloro-2-thia-cyclopenta[a]inden-8-one. [Formula (I): R$^2$=Cl; R$^1$=R$^3$=R$^4$=R$^5$=R$^6$=H; R$^9$+R$^{10}$=O]

To a suspension of 2-(6-chloro-8-oxo-8H-2-thia-cyclopenta[a]inden-1-yl)-isoindol e-1,3-dione (0.45 mmol, Example 9, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 10

Part A: 3-(2-Methylphenyl)-2-cyano-but-2-enoic acid ethyl ester

A mixture of 2'-methylacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(2-methylphenyl)-thiophene-3-carboxylic acid ethyl ester

The mixture of E and Z-isomers of 2-cyano-3-(2-methylphenyl)-but-2-enoic acid ethyl ester (39.5 mmol, Example 10, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a column of silica gel to afford the desired product.

Part C: 2-(1,3-Dioxo-1,3-dihydroisoindol-2-yl)-4-(2-methylphenyl)-thiophene-3-carboxylic acid ethyl ester A mixture of 2-amino-4-(2-methylphenyl)-thiophene-3-carboxylic acid ethyl ester (2 mmol, Example 10, Part C) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization affords the desired product.

Part D: 2-(1,3-Dioxo-1,3-dihydroisoindol-2-yl)-4-(2-methylphenyl)-thiophene-3-carboxylic acid To a solution of NaOH (1.4 mmol) in a 1:1 mixture of methanol:H$_2$O (6 mL) is added 2-(1,3-dioxo-1,3-dihydroisoindol-2-yl)-4-(2-methylphenyl)-thiophene-3-carboxylic acid ethyl ester (0.7 mmol, Example 10, Part D). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(4-Methyl-8-oxo-8H-2-thia-cyclopenta[a]inden-1-yl)-isoindole-1,3-dione A suspension of 2-(1,3-dioxo-1,3-dihydroisoindol-2-yl)-4-(2-methylphenyl)-thiophene-3-carboxylic acid (1.15 mmol, Example 10, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-4-methyl-2-thia-cyclopenta[a]inden-8-one. [Formula (I): R$^4$=CH$_3$; R$^1$=R$^2$=R$^3$=R$^5$=R$^6$=H; R$^9$+R$^{10}$=O]

To a suspension of 2-(6-chloro-8-oxo-8H-2-thia-cyclopenta[a]inden-1-yl)-isoindole-1,3-dione (0.45 mmol, Example 10, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 11

Part A: 3-(4-Methylphenyl)-2-cyano-but-2-enoic acid ethyl ester

A mixture of 4'-methylacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(4-methylphenyl)-thiophene-3-carboxylic acid ethyl ester

The mixture of E and Z-isomers of 2-cyano-3-(4-methylphenyl)-but-2-enoic acid ethyl ester (39.5 mmol, Example 11, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 2-(1,3-Dioxo-1,3-dihydroisoindol-2-yl)-4-(4-methylphenyl)-thiophene-3-carboxylic acid ethyl ester A mixture of 2-amino-4-(4-methylphenyl)-thiophene-3-carboxylic acid ethyl ester (2 mmol, Example 11, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 2-(1,3-Dioxo-1,3-dihydroisoindol-2-yl)-4-(4-methylphenyl)-thiophene-3-carboxylic acid To a solution of NaOH (1.4 mmol) in a 1:1 mixture of methanol:$H_2O$ (6 mL) is added 2-(1,3-dioxo-1,3-dihydroisoindol-2-yl)-4-(4-methylphenyl)-thiophene-3-carboxylic acid ethyl ester (0.7 mmol, Example 11, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(6-Methyl-8-oxo-8H-2-thia-cyclopenta[a]inden-1-yl)-isoindole-1,3-dione A suspension of 2-(1,3-dioxo-1,3-dihydroisoindol-2-yl)-4-(4-methylphenyl)-thiophene-3-carboxylic acid (1.15 mmol, Example 11, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 1-Amino-6-methyl-2-thia-cyclopenta[a]inden-8-one. [Formula (I): $R^2=CH_3$; $R^1=R^3=R^4=R^5=R^6=H$; $R^9+R^{10}=O$]

To a suspension of 2-(6-methyl-8-oxo-8H-2-thia-cyclopenta[a]inden-1-yl)-isoindole-1,3-dione (0.45 mmol, Example 11, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 12

Part A: 3-(4-Ethylphenyl)-2-cyano-but-2-enoic acid ethyl ester

A mixture of 4'-ethylacetophenone (50 mmol), ethyl cyanoacetate (50 mmol), acetic acid (1.14 mL), ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(4-ethylphenyl)thiophene-3-carboxylic acid ethyl ester

The mixture of E and Z-isomers of 2-cyano-3-(4-ethylphenyl)-but-2-enoic acid ethyl ester (39.5 mmol, Example 12, Part A), morpholine (39.5 mmol), and sulfur (39.5 10 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 2-(1,3-Dioxo-1,3-dihydroisoindol-2-yl)-4-(4-ethylphenyl)-thiophene-3-carboxylic acid ethyl ester A mixture of 2-amino-4-(4-ethylphenyl)-thiophene-3-carboxylic acid ethyl ester (2 mmol, Example 12, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 2-(1,3-Dioxo-1,3-dihydroisoindol-2-yl)-4-(4-ethylphenyl)-thiophene-3-carboxylic acid To a solution of NaOH (1.4 mmol) in a 1:1 mixture of methanol:$H_2O$ (6 mL) is added 2-(1,3-dioxo-1,3-dihydroisoindol-2-yl)-4-(4-ethylphenyl)-thiophene-3-carboxylic acid ethyl ester (0.7 mmol, Example 12, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(6-Ethyl-8-oxo-8H-2-thia-cyclopenta[a]inden-1-yl)-isoindole-1,3-dione

A suspension of 2-(1,3-dioxo-1,3-dihydroisoindol-2-yl)-4-(4-ethylphenyl)-thiophene-3-carboxylic acid (1.15 mmol, Example 12, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 1-Amino-6-ethyl-2-thia-cyclopenta[a]inden-8-one. [Formula (I): $R^2=CH_2CH_3$; $R^1=R^3=R^4=R^5=R^6=H$; $R^9+R^{10}=O$]

To a suspension of 2-(6-ethyl-8-oxo-8H-2-thia-cyclopenta[a]inden-1-yl)-isoindole-1,3-dione (0.45 mmol, Example 12, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 13

Part A:
3-[2-(Carboxamido)phenyl]-2-cyano-but-2-enoic acid ethyl ester

A mixture of 2'-(carboxamido)acetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-[2-(carboxamido)phenyl]-thiophene-3-carboxylic acid ethyl ester The mixture of E and Z-isomers of 3-[2-(carboxamido)phenyl]-2-cyano-but-2-enoic acid ethyl ester (39.5 mmol, Example 13, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 2-(1,3-Dioxo-1,3-dihydroisoindol-2-yl)-4-[2-(carboxamido)phenyl]-thiophene-3-carboxylic acid ethyl ester A mixture of 2-amino-4-[2-(carboxamido)phenyl]-thiophene-3-carboxylic acid ethyl ester (2 mmol, Example 13, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 4-[2-(Carboxamido)phenyl]-2-(1,3-dioxo-1, 3-dihydroisoindol-2-yl)-thiophene-3-carboxylic acid To a solution of NaOH (1.4 mmol) in a 1:1 mixture of methanol:H$_2$O (6 mL) is added 2-(1,3-dioxo-1,3-dihydroisoindol-2-yl)-4-[2-(carboxamido)phenyl]-thiophene-3-carboxylic acid ethyl ester (0.7 mmol, Example 13, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-[4-(Carboxamido)-8-oxo-8H-2-thia-cyclopenta[a]inden-1-yl]-isoindole-1,3-dione A suspension of 4-[2-(carboxamido)phenyl]-2-(1,3-dioxo-1,3-dihydroisoindol-2yl)-thiophene-3-carboxylic acid (1.15 mmol, Example 13, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-4-(carboxamido)-2-thia-cyclopenta[a]inden-8-one. [Formula (I): R$^4$=C(O)NH$_2$; R$^1$=R$^2$=R$^3$=R$^5$=R$^6$=H; R$^9$+R$^{10}$=O]

To a suspension of 2-(4-(carboxamido)-8-oxo-8H-2-thia-cyclopenta[a]inden-1-yl)-isoindole-1,3-dione (0.45 mmol, Example 13, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLES 14 AND 15

Part A: 3-[3-(Carboxamido)phenyl]-2-cyano-but-2-enoic acid ethyl ester

A mixture of 3'-(carboxamido)-acetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-[3-(carboxamido)phenyl]-thiophene-3-carboxylic acid ethyl ester The mixture of E and Z-isomers of 2-cyano-3-[3-(carboxamido)phenyl]-but-2-enoic acid ethyl ester (39.5 mmol, Example 14 & 15, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a column of silica gel to afford the desired product.

Part C: 4-[3-(Carboxamido)phenyl]-2-(1,3-dioxo-1, 3-dihydroisoindol-2-yl)-thiophene-3-carboxylic acid ethyl ester A mixture of 2-amino-4-[3-(carboxamido)phenyl]-thiophene-3-carboxylic acid ethyl ester (2 mmol, Example 14 & 15, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization affords the desired product.

Part D: 4-[3-(Carboxamido)phenyl]-2-(1,3-dioxo-1, 3-dihydroisoindol-2-yl)-thiophene-3-carboxylic acid To a solution of NaOH (1.4 mmol) in a 1:1 mixture of methanol:H$_2$O (6 mL) is added 4-[3-(carboxamido)phenyl]-2-(1,3-dioxo-1,3-dihydroisoindol-2-yl)thiophene-3-carboxylic acid ethyl ester (0.7 mmol, Example 14 & 15, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-[5-(Carboxamido)-8-oxo-8H-2-thia-cyclopenta[a]inden-1-yl]-isoindole-1,3-dione and 2-[7-(Carboxamido)-8-oxo-8H-2-thia-cyclopenta[a]inden-1-yl]-isoindole-1,3-dione A suspension of 2-(1,3-dioxo-1,3-dihydroisoindol-2-yl)-4-[3 (carboxamido)phenyl]-thiophene-3-carboxylic acid (1.15 mmol, Example 14 & 15, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

EXAMPLE 14

Part F: 1-Amino-5-(carboxamido)-2-thia-cyclopenta[a]inden-8-one. [Formula (I): $R^3$=C(O)$NH_2$; $R^1$=$R^2$=$R^4$=$R^5$=$R^6$=H; $R^9$+$R^{10}$=O]; and

EXAMPLE 15

Part F: 1-Amino-7-(carboxamido)-2-thia-cyclopenta[a]inden-8-one. [Formula (I): $R^1$=C(O)$NH_2$; $R^2$=$R^3$$R^4$=$R^5$=$R^6$=H; $R^9$+$R^{10}$=O]

To a mixture of 2-[5-(carboxamido)-8-oxo-8H-2-thia-cyclopenta[a]inden-1-yl)-isoindole-1,3-dione and 2-[7-(trifluoromethyl)-8-oxo-8H-2-thia-cyclopenta[a]inden-1-yl)-isoindole-1,3-dione (0.45 mmol, Example 14 & 15, Part E) suspended in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel. Fractions containing the individual products are pooled, evaporated, and each product is recrystallized.

EXAMPLE 16

Part A:
3-[4-(Carboxamido)phenyl]-2-cyano-but-2-enoic acid ethyl ester

A mixture of 4'-(carboxamido)acetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-[4-(carboxamido)phenyl]-thiophene-3-carboxylic acid ethyl ester The mixture of E and Z-isomers of 2-cyano-3-[4-(carboxamido)phenyl]-but-2-enoic acid ethyl ester (39.5 mmol, Example 16, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 4-[4-(Carboxamido)phenyl]-2-(1,3-dioxo-1,3-dihydroisoindol-2-yl)-thiophene-3-carboxylic acid ethyl ester A mixture of 2-amino-4-[4-(carboxamido)phenyl]-thiophene-3-carboxylic acid ethyl ester (2 mmol, Example 16, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water 10 (10 mL), brine (10 mL), dried ($Na_2SO_4$), filtered, and concentrated in vacuo. Recrystallization affords the desired product.

Part D: 4-(4-Carboxamidophenyl)-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-[4-(carboxamido)phenyl]-2-(1,3-dioxo-1,3-dihydroisoindol-2-yl)-thiophen e-3-carboxylic acid ethyl ester (0.7 mmol, Example 16, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(6-Carboxamido-8-oxo-8H-2-thia-cyclopenta[a]inden-1-yl)-isoindole-1,3-dione A suspension of 4-[4-(carboxamido)phenyl]-2-(1,3-dioxo-1,3-dihydroisoindol-2-yl)-thiophene-3-carboxylic acid (1.15 mmol, Example 16, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 1-Amino-6-carboxamido-2-thia-cyclopenta[a]inden-8-one. [Formula (I): $R^2$=C(O)NH$_2$; $R^1$=$R^3$=$R^4$=$R^5$=$R^6$=H; $R^9$+$R^{10}$=O]

To a suspension of 2-(6-carboxamido-8-oxo-8H-2-thia-cyclopenta[a]inden-1-yl)-isoindole-1,3-dione (0.45 mmol, Example 16, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 17

Part A: 2-Cyano-3-(2-methoxyphenyl)-but-2-enoic acid ethyl ester

A mixture of 2'-methoxyacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(2-methoxyphenyl)-thiophene-3-carboxylic acid ethyl ester

The mixture of E and Z-isomers of 2-cyano-3-(2-methoxyphenyl)-but-2-enoic acid ethyl ester (39.5 mmol, Example 17, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a column of silica gel to afford the desired product.

Part C: 2-(1,3-Dioxo-1,3-dihydroisoindol-2-yl)-4-(2-methoxyphenyl)-thiophene-3-carboxylic acid ethyl ester A mixture of 2-amino-4-(2-methoxyphenyl)-thiophene-3-carboxylic acid ethyl ester (2 mmol, Example 17, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization affords the desired product.

Part D: 2-(1,3-Dioxo-1,3-dihydroisoindol-2-yl)-4-(2-methoxyphenyl)-thiophene-3-carboxylic acid To a solution of NaOH (1.4 mmol) in a 1:1 mixture of methanol:H$_2$O (6 mL) is added 2-(1,3-dioxo-1,3-dihydroisoindol-2-yl)-4-(2-methoxyphenyl)-thiophene-3-carboxylic acid ethyl ester (0.7 mmol, Example 17, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-[4-Methoxy-8-oxo-8H-2-thia-cyclopenta[a]inden-1-yl)-isoindole-1,3-dione A suspension of 2-(1,3-dioxo-1,3-dihydroisoindol-2-yl)-4-(2-methoxyphenyl)-thiophene-3-carboxylic acid (1.15 mmol, Example 17, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride. The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-4-methoxy-2-thia-cyclopenta[a]inden-8-one. [Formula (I): $R^4$=OCH$_3$; $R^1$=$R^2$=$R^3$=$R^5$=$R^6$=H; $R^9$+$R^{10}$=O]

To a suspension of 2-(4-methoxy-8-oxo-8H-2-thia-cyclopenta[a]inden-1-yl)-isoindole-1,3-dione (0.45 mmol, Example 17, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether and ethyl acetate. Fractions containing the product are collected, evaporated, and the product recrystallized.

EXAMPLES 18 AND 19

Part A: 2-Cyano-3-[3-methoxyphenyl]-but-2-enoic acid ethyl ester

A mixture of 3'-methoxyacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B:
2-Amino-4-(3-methoxyphenyl)-thiophene-3-carboxylic acid ethyl ester

The mixture of E and Z-isomers of 2-cyano-3-(3-methoxyphenyl)-but-2-enoic acid ethyl ester (39.5 mmol, Example 18 & 19, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 2-(1,3-Dioxo-1,3-dihydroisoindol-2-yl)-4-(3-methoxyphenyl)-thiophene-3-carboxylic acid ethyl ester A mixture of 2-amino-4-(3-methoxyphenyl)-thiophene-3-carboxylic acid ethyl ester (2 mmol, Example 18 & 19, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried (Na2SO4), filtered, and concentrated in vacuo. Recrystallization affords the desired product.

Part D: 2-(1,3-Dioxo-1,3-dihydroisoindol-2-yl)-4-(3-methoxyphenyl)-thiophene-3-carboxylic acid To a solution of NaOH (1.4 mmol) in a 1:1 mixture of methanol:$H_2O$ (6 mL) is added 2-(1,3-dioxo-1,3-dihydroisoindol-2-yl)-4-(3-methoxyphenyl)-thiophene-3-carboxylic acid ethyl ester (0.7 mmol, Example 18 & 19, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-[5-Methoxy-8-oxo-8H-2-thia-cyclopenta[a]inden-1-yl]-isoindole-1,3-dione and 2-[7-Methoxy-8-oxo-8H-2-thia-cyclopenta[a]inden-1-yl]-isoindole-1,3-dione A suspension of 2-(1,3-dioxo-1,3-dihydroisoindol-2-yl)-4-(3-methoxyphenyl)-thiophene-3-carboxylic acid (1.15 mmol, Example 18 & 19, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

EXAMPLE 18

Part F: 1-Amino-5-methoxy-2-thia-cyclopenta[a]inden-8-one. [Formula (I): $R^3$=$OCH_3$; $R^1$=$R^2$=$R^3$=$R^5$=$R^6$=H; $R^9$+$R^{10}$=O]; and

EXAMPLE 19

Part F: 1-Amino-7-methoxy-2-thia-cyclopenta[a]inden-8-one. [Formula (I): $R^1$=$OCH_3$; $R^2$=$R^3$=$R^4$=$R^5$=$R^6$=H; $R^9$+$R^{10}$=O]

To a mixture of 2-[5-methoxy-8-oxo-8H-2-thia-cyclopenta[a]inden-1-yl)-isoindole-1,3-dione and 2-[7-methoxy-8-oxo-8H-2-thia-cyclopenta[a]inden-1-yl)-isoindole-1,3-dione (0.45 mmol, Example 18 & 19, Part E) suspended in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel. Fractions containing the individual products are pooled, evaporated, and each product is recrystallized.

EXAMPLE 20

Part A: 2-Cyano-3-(4-methoxyphenyl)-but-2-enoic acid ethyl ester

A mixture of 4'-methoxyacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B:
2-Amino-4-(4-methoxyphenyl)-thiophene-3-carboxylic acid ethyl ester

The mixture of E and Z-isomers of 2-cyano-3-(4-methoxyphenyl)-but-2-enoic acid ethyl ester (39.5 mmol, Example 20, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a column of silica gel to afford the desired product.

Part C: 2-(1,3-Dioxo-1,3-dihydroisoindol-2-yl)-4-(4-methoxyphenyl)-thiophene-3-carboxylic acid ethyl ester A mixture of 2-amino-4-(4-methoxyphenyl)-thiophene-3-carboxylic acid ethyl ester (2 mmol, Example 20, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization affords the desired product.

Part D: 2-(1,3-Dioxo-1,3-dihydroisoindol-2-yl)-4-(4-methoxyphenyl)-thiophene-3-carboxylic acid To a solution of NaOH (1.4 mmol) in a 1:1 mixture of methanol:H$_2$O (6 mL) is added 2-(1,3-dioxo-1,3-dihydroisoindol-2-yl)-4-(4-methoxyphenyl)-thiophene-3-carboxylic acid ethyl ester (0.7 mmol, Example 20, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-[6-Methoxy-8-oxo-8H-2-thia-cyclopenta[a]inden-1-yl]-isoindole-1,3-dione A suspension of 2-(1,3-dioxo-1,3-dihydroisoindol-2-yl)-4-(4-methoxyphenyl)-thiophene-3-carboxylic acid (1.15 mmol, Example 20, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-6-methoxy-2-thia-cyclopenta[a]inden-8-one. [Formula (I): R$^2$=OCH$_3$; R$^1$=R$^3$=R$^4$=R$^5$=R$^6$=H; R$^9$+R$^{10}$=O]

To a suspension of 2-[6-methoxy-8-oxo-8H-2-thia-cyclopenta[a]inden-1-yl]-isoindole-1,3-dione (0.45 mmol, Example 20, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 21

Part A: 3-[4-Bromophenyl]-2-cyano-but-2-enoic acid ethyl ester

A mixture of 4'-bromoacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(4-bromophenyl)-thiophene-3-carboxylic acid ethyl ester

The mixture of E and Z-isomers of 3-(4-bromophenyl)-2-cyano-but-2-enoic acid ethyl ester (39.5 mmol, Example 21, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried (Na$_2$SO$_4$), filtered, and concentrated. The residue is chromatographed on a 20 column of silica gel to afford the desired product.

Part C: 4-(4-Bromophenyl)-2-(1,3-dioxo-1,3-dihydroisoindol-2-yl)-thiophene-3-carboxylic acid ethyl ester A mixture of 2-amino-4-(4-bromophenyl)-thiophene-3-carboxylic acid ethyl ester (2 mmol, Example 21, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous NaHCO$_3$ (10 mL), water (10 mL), brine (10 mL), dried (Na$_2$SO$_4$), filtered, and concentrated in vacuo. Recrystallization affords the desired product.

Part D: 4-(4-Bromophenyl)-2-(1,3-dioxo-1,3-dihydroisoindol-2-yl)-thiophene-3-carboxylic acid To a solution of NaOH (1.4 mmol) in a 1:1 mixture of methanol:H$_2$O (6 mL) is added 4-(4-bromophenyl)-2-(1,3-dioxo-1,3-dihydroisoindol-2-yl)-thiophene-3-carboxylic acid ethyl ester (0.7 mmol, Example 21, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(6-Bromo-8-oxo-8H-2-thia-cyclopenta[a]inden-1-yl)-isoindole-1,3-dione

A suspension of 4-(4-bromophenyl)-2-(1,3-dioxo-1,3-dihydroisoindol-2-yl)thiophene-3-carboxylic acid (1.15 mmol, Example 21, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried (Na$_2$SO$_4$), filtered, and concentrated. The residue is applied to a short column of silica gel, eluting with ethyl acetate, to afford the desired product.

Part F: 1-Amino-6-bromo-2-thia-cyclopenta[a]inden-8-one. [Formula (I): R$^2$=Br; R$^1$=R$^3$=R$^4$=R$^5$=R$^6$=H; R$^9$+R$^{10}$=O]

To a suspension of 2-(6-bromo-8-oxo-8H-2-thia-cyclopenta[a]inden-1-yl)-isoindole-1,3-dione (0.45 mmol, Example 21, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 22

1-Amino-5-chloro-8-hydroxy-2-thia-cyclopenta[a]indene. [Formula (I): R$^3$=Cl; R$^1$=R$^2$=R$^4$=R$^5$=R$^6$=H; R$^9$=H; R$^{10}$=OH]

To a solution of 1-amino-5-chloro-2-thia-cyclopenta[a]inden-8-one (1.0 mmol, Example 5) in methanol (10 mL) is added sodium borohydride (1.2 mmol) at 5° C. After the addition is complete, the mixture is heated to reflux for 6 hours, cooled to room temperature, made acidic by the dropwise addition of 1 N HCl, then concentrated in vacuo. The residue is partitioned between ethyl acetate and water, the organic extracts combined, washed once with brine, then dried (MgSO$_4$), filtered, and evaporated. The residue is purified by column chromatography, eluting with a mixture of ethyl acetate and petroleum ether. Fractions containing the product are collected, evaporated, and the product recrystallized.

EXAMPLE 23

1-Acetylamino-5-chloro-2-thia-cyclopenta[a]inden-8-one. [Formula (I): R$^3$=Cl; R$^1$=R$^2$=R$^4$=R$^5$=H; R$^6$=C(O)CH$_3$; R$^9$+R$^{10}$=O]

1-Amino-5-chloro-2-thia-cyclopenta[a]inden-8-one (1.0 mmol, Example 5) is dissolved in anhydrous pyridine (10 mL). The solution is cooled to 5° C., then 4-(dimethylamino)-pyridine (1 mg) and acetic anhydride (1.1 mmol) are added. The mixture is allowed to warm to room temperature over 4 hours, then stirred an additional 16 hours at room temperature. The mixture is concentrated in vacuo, co-evaporated with ethanol to remove the last traces of pyridine, and purified by column chromatography on silica gel, eluting with a mixture of ethyl acetate and petroleum ether. Fractions containing the desired product are collected and evaporated.

EXAMPLE 24

1,6-Diamino-2-thia-cyclopenta[a]inden-8-one. [Formula (I): R$^2$=NH$_2$; R$^1$=R$^3$=R$^4$=R$^5$=R$^6$=H; R$^9$+R$^{10}$=O]

To a suspension of 1-amino-6-carboxamido-2-thia-cyclopenta[a]inden-8-one (1.0 mmol, Example 16) in THF:H$_2$O (10 mL) at 0° C., is added 2 M NaOH (2 mL). The mixture is then treated dropwise with bromine until the color persists for 10 min. The mixture is then stirred an additional hour at 0° C., warmed to room temperature, and concentrated in vacuo. The residue is purified by column chromatography on silica gel, fractions containing the desired product combined, evaporated to dryness and the product recrystallized.

EXAMPLE 25

Part A: 2-cyano-3-(2,3-dichlorophenyl)-but-2-enoic acid ethyl ester

A mixture of 2',3'-dichloroacetophenone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried (Na$_2$SO$_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-(2,3-dichlorophenyl)-thiophene-3-carboxylic acid ethyl ester.

The mixture of E and Z-isomers of 2-cyano-3-(2,3-dichlorophenyl)-but-2-enoic acid ethyl ester (39.5 mmol, Example 25, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 4-(2,3-Dichlorophenyl)-2-(1,3-dioxo-1,3-dihydroisoindol-2-yl)-thiophene-3-carboxylic acid ethyl ester A mixture of 2-amino-4-(2,3-dichlorophenyl)thiophene-3-carboxylic acid ethyl ester (2 mmol, Example 25, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 4-(2,3-Dichlorophenyl)-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-(2,3-dichlorophenyl)-2-(1,3-dioxo-1,3-dihydroisoindol-2-yl)-thiophene-3-carboxylic acid ethyl ester (0.7 mmol, Example 25, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 2-(4,5-Dichloro-8-oxo-8H-2-thia-cyclopenta[a]inden-1-yl)-isoindole-1,3-dione A suspension of 4-(2,3-dichlorophenyl)-2-(1,3-dioxo-1,3-dihydroisoindol-2-yl)-thiophene-3-carboxylic acid (1.15 mmol, Example 25, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 1-Amino-4,5-dichloro-2-thia-cyclopenta[a]inden-8-one. [Formula (I): $R^3=R^4=Cl$; $R^1=R^2=R^5=R^6=H$; $R^9+R^{10}=O$]

To a suspension of 2-(4,5-dichloro-8-oxo-8H-2-thia-cyclopenta[a]inden-1-yl)-isoindole-1,3-dione (0.45 mmol, Example 25, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether and ethyl acetate. Fractions containing the product are collected, evaporated, and the product recrystallized.

EXAMPLE 26

Part A: Diethyl 2-oxo-3-(3-chlorophenyl)succinate

The title compound is prepared according to the method of Klioze and Ehrgott (U.S. Pat. No. 4,216,218) from diethyl oxalate and ethyl(3-chlorophenyl)acetate.

Part B: Ethyl 2-(3-chlorophenyl)acrylate

The title compound is prepared according to the method of Klioze and Ehrgott (U.S. Pat. No. 4,216,218) from formaldehyde and diethyl 2-oxo-3-(3-chlorophenyl)succinate (Example 26, Part A).

Part C: Ethyl 3-(benzylamino)propionate

The title compound is prepared according to the method of Klioze and Ehrgott (U.S. Pat. No. 4,216,218) from ethyl acrylate and benzylamine.

Part D: Ethyl 3-benzylamino-2-(3-chlorophenyl)-N-(2-ethoxycarbonylethyl)propionate This compound is prepared according to the method of Klioze and Ehrgott (U.S. Pat. No. 4,216,218) from ethyl 3-(benzylamino)propionate (Example 26, Part C) and ethyl 2-(3-chlorophenyl)acrylate (Example 26, Part B).

Part E: 1-Benzyl-3-(3-chlorophenyl)-4-piperidone

The title compound is prepared according to the method of Klioze and Ehrgott (U.S. Pat. No. 4,216,218) from ethyl 3-benzylamino-2-(3-chlorophenyl)-N-(2-ethoxycarbonylethyl)-propionate (Example 26, Part D).

Part F: 1-Benzyl-3-(3-chlorophenyl)-3-methyl-4-piperidone

A solution of 1-benzyl-3-(3-chlorophenyl)-4-piperidone (75 mmol) in anhydrous THF (250 mL) is cooled to −30° C., then treated with a solution of freshly prepared lithium diisopropylamide (2.0 M in THF/heptane, 45 mL). After stirring for 15 min, a solution of methyl iodide (80 mmol) in THF (40 mL) is rapidly added. The mixture is then stirred for 1 hour at −30° C., warmed quickly to room temperature, and quenched with a saturated aqueous solution of ammonium chloride. The organic layer is collected, washed with water, brine, and dried ($MgSO_4$). After filtering, the filtrate is concentrated in vacuo to afford the desired intermediate.

Part G: Ethyl 2-(1-benzyl-3-(3-chlorophenyl)-3-methyl-4-piperidinylidene)-5-cyanoacetate A mixture of 1-benzyl-3-(3-chlorophenyl)-3-methyl-4-piperidone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part H: 2-Amino-6-benzyl-4-(3-chlorophenyl)-4-methyl-4,5,6,7-tetrahydrothieno[2,3-c]pyridin-3-yl]-carboxylic acid ethyl ester The mixture of E and Z-isomers of ethyl 2-(1-benzyl-3-(3-chlorophenyl)-3-methyl-4-piperidinylidene)-2-cyanoacetate (39.5 mmol, Example 26, Part G), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part I: 6-Benzyl-4-(3-chlorophenyl)-2-(1,3-dioxo-1,3-dihydroisoindol-2-yl)-4-methyl-4,5,6,7-tetrahydrothieno[2,3-c]pyridin-3-yl]-carboxylic acid ethyl ester A mixture of 2-amino-6-benzyl-4-(3-chlorophenyl)-4-methyl-4,5,6,7-tetrahydrothieno[2,3-c]pyridin-3-yl]-carboxylic acid ethyl ester (2 mmol, Example 26, Part H) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part J: 6-Benzyl-4-(3-chlorophenyl)-2-(1,3-dioxo-1,3-dihydroisoindol-2-yl)-4-methyl-4,5,6,7-tetrahydrothieno[2,3-c]pyridin-3-yl]-carboxylic acid To a solution of NaOH (1.4 mmol) in a 1:1 mixture of methanol:$H_2O$ (6 mL) is added 6-benzyl-4-(3-chlorophenyl)-2-(1,3-dioxo-1,3-dihydroisoindol-2-yl)-4-methyl 4,5,6,7-tetrahydrothieno[2,3-c]pyridin-3-yl]-carboxylic acid ethyl ester (0.7 mmol, Example 26, Part I). The mixture is heated to reflux for 90 min, then diluted with water (12 mL), chilled in an ice bath, and acidified with concentrated HCl. The product that precipitates is collected by filtration, washed with water, and dried, affording the desired compound.

Part K: 2-(2-Benzyl-9-chloro-6-oxo-6H-1,2,3,10b-tetrahydro-benzo[h]thieno[2,3,4-de]isoquinolin-5-yl)-isoindole-1,3-dione A suspension of 6-benzyl-4-(3-chlorophenyl)-2-(1,3-dioxo-1,3-dihydroisoindol-2-yl)-4-methyl-4,5,6,7-tetrahydrothieno[2,3-c]pyridin-3-yl]-carboxylic acid (1.15 mmol, Example 26, Part J) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part L: 5-Amino-2-benzyl-9-chloro-1,2,3,10b-tetrahydro-6H-benzo[h]thieno[2,3,4-de]isoquinolin-6-one. [Formula (VIII): X=Cl; $X^1$=H; $X^2$=$NH_2$].

To a suspension of 2-(2-Benzyl-9-chloro-oxo-6H-1,2,3,10b-tetrahydro-benzo[h]thieno[2,3,4-de]isoquinolin-5-yl)-isoindole-1,3-dione (0.45 mmol, Example 26, Part K) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLES 27 AND 28

Part A: 2-Acetyl-2-(3-chlorophenyl)-1,3-dithiane

To a solution of 3-chlorobenzaldehyde (100 mmol) in chloroform (250 mL) is added 1,3-propanedithiol (110 mmol). The mixture is chilled to −10° C. and HCl gas is gently bubbled through the mixture for 20 min. The mixture is stirred at −10° C. for one hour, then allowed to warm to room temperature overnight. The solution is washed with 1 M KOH, water, brine, and dried ($K_2CO_3$). After filtering, the organic extract is concentrated in vacuo to afford 2-(3-chlorophenyl)-1,3-dithiane.

The crude 2-(3-chlorophenyl)-1,3-dithiane is dissolved in anhydrous THF (400 mL). After chilling to −78° C., a solution of n-butyl lithium (2.5 Molar, 42 mL) is added slowly by syringe. The solution is stirred for 30 min at −78° C., followed by the addition of acetyl chloride. The mixture is warmed to room temperature, quenched by the addition of a saturated aqueous solution of $NH_4Cl$, washed with water, brine, and dried ($Na_2SO_4$). After removing the dessicant, the filtrate was concentrated in vacuo to provide the desired product.

Part B: 4-(3-Chlorophenyl)-2-cyano-3-methyl-4-(1,3-dithian-2-yl)but-2-enoic acid ethyl ester A mixture of 2-acetyl-2-(3-chlorophenyl)-1,3-dithiane (50 mmol, Example 27 & 28, Part A), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part C: 2-Amino-4-[2-(3-chlorophenyl)-1,3-dithian-2-yl]thiophene-3-carboxylic acid ethyl ester The mixture of E and Z-isomers of 4-(3-chlorophenyl)-2-cyano-3-methyl-4-(1,3-dithian-2-yl)but-2-enoic acid ethyl ester (39.5 mmol, Example 27 & 28, Part B), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part D: 4-[2-(3-Chlorophenyl)-1,3-dithian-2-yl]-2-(1,3-dioxo-1,3-dihydroisoindol-2-yl)-thiophene-3-carboxylic acid ethyl ester A mixture of 2-amino-4-[2-(3-chlorophenyl)-1,3-dithian-2-yl]thiophene-3-carboxylic acid ethyl ester (2 mmol, Example 27 & 28, Part C) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part E: 4-[2-(3-Chlorophenyl)-1,3-dithian-2-yl]-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-[2-(3-chlorophenyl)-1,3-dithian-2-yl]-2-(1,3-dioxo-1,3-dihydroisoindol-2-yl)-thiophene-3carboxylic acid ethyl ester (0.7 mmol, Example 27 & 28, Part D). The mixture is heated to reflux for 90 min, then diluted with water (12 mL), chilled in an ice bath, and acidified with concentrated HCl. The product that precipitates is collected by filtration, washed with water, and dried, affording the desired compound.

Part F: 2-[5-Chloro-4-oxo-9-spiro(1,3-dithian-2-yl)-9H-naphtho[2,3-c]thiophene-3-yl]-isoindole-1,3-dione and 2-[7-chloro-4-oxo-9-spiro(1,3-dithian-2-yl)-9H-naphtho[2,3-c]thiophene-3-yl]-isoindole-1,3-dione A suspension of 4-[2-(3-chlorophenyl)-1,3-dithian-2-yl]-2-(1,3-dioxo-1,3-dihydroisoindol-2-yl)-thiophene-3-carboxylic acid (1.15 mmol, Example 27 & 28, Part 25 E) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

EXAMPLE 27

Part G: 3-Amino-5-chloro-9-spiro(1,3-dithian-2-yl)-9H-naphtho[2,3-c]thiophene-4-one. [Formula (II): $R^1$=Cl; $R^2$=$R^3$=$R^4$=$R^5$=$R^6$=H; $R^7$+$R^8$=(1,3-dithian-2-yl); $R^9$+$R^{10}$=O]; and

EXAMPLE 28

Part G: 3-Amino-7-chloro-9-spiro(1,3-dithian-2-yl)-9H-naphtho[2,3-c]thiophene-4-one. [Formula (II): $R^3$=Cl; $R^1$=$R^2$=$R^4$=$R^5$=$R^3$=H; $R^7$+$R^8$=(1,3-dithian-2-yl); $R^9$+$R^{10}$=O]

To a suspension of 2-[5-chloro-4-oxo-9-spiro(1,3-dithian-2-yl)-9H-naphtho[2,3-c]thiophene-3-yl]-isoindole-1,3-dione and 2-[7-chloro-4-oxo-9-spiro(1,3-dithian-2-yl)-9H-naphtho[2,3-c]thiophene-3-yl]-isoindole-1,3-dione (0.45 mmol, Example 27 & 28, Part F) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 29

3-Amino-7-chloro-9H-naphtho[2,3-c]thiophene-4-one. [Formula (II): $R^3$=Cl; $R^1$=$R^2$=$R^4$=$R^5$=$R^6$=$R^7$=$R^8$=H; $R^9$+$R^{10}$=O]

A solution of 3-amino-7-chloro-9-spiro(1,3-dithian-2-yl)-9H-naphtho[2,3-c]thiophene-4-one (0.5 mmol) in methanol is treated with excess Raney nickel at reflux for 24 hours. After cooling to room temperature, the catalyst is removed, the filtrate concentrated in vacuo, and the product purified by column chromatography on silica gel.

EXAMPLE 30

Part A:
5-[4-Bromophenyl]-2-cyano-3-ethyl-pent-2-enoic acid ethyl ester

A mixture of 5-(4-bromophenyl)pentanone (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-[2-(4-bromophenyl)ethyl]-5-methyl-thiophene-3-carboxylic acid ethyl ester The mixture of E and Z-isomers of 5-[4-bromophenyl]-2-cyano-3-ethyl-pent-2-enoic acid ethyl ester (39.5 mmol, Example 30, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 4-[2-(4-Bromophenyl)ethyl]-2-(1,3-dioxo-1,3-dihydroisoindol-2-yl)-5-methyl-thiophene-3-carboxylic acid ethyl ester A mixture of 2-amino-4-[2-(4-bromophenyl)ethyl]-5-methyl-thiophene-3-carboxylic acid ethyl ester (2 mmol, Example 30, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 4-[2-(4-Bromophenyl)ethyl]-2-(1,3-dioxo-1,3-dihydroisoindol-2-yl)-5-methyl-thiophene-3-carboxylic acid To a solution of NaOH (1.4 mmol) in a 1:1 mixture of methanol:$H_2O$ (6 mL) is added 4-[2-(4-bromophenyl)ethyl]-2-(1,3-dioxo-1,3-dihydroisoindol-2-yl)-5-methy-thiophene-3-carboxylic acid ethyl ester (0.7 mmol, Example 30, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 6-Bromo-9,10-dihydro-3-(1,3-dioxo-1,3-dihydroisoindol-2-yl)-1-methyl-2-thia-benzo[f]azulen-4-one A suspension of 4-[2-(4-bromophenyl)ethyl]-2-(1,3-dioxo-1,3-dihydroisoindol-2-yl)-5-methyl-thiophene-3-carboxylic acid (1.15 mmol, Example 30, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 3-Amino-6-bromo-9,10-dihydro-1-methyl-2-thia-benzo[f]azulen-4-one. [Formula (III): $R^2$=Br; $R^5$=$CH_3$; $R^1$=$R^3$=$R^4$=$R^6$=$R^7$=$R^8$=H; $R^9$+$R^{10}$=O]

To a suspension of 6-bromo-9,10-dihydro-3-(1,3-dioxo-1,3-dihydroisoindol-2yl)-1-methyl-2-thia-benzo[f]azulen-4-one (0.45 mmol, Example 30, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 31

Part A: 5-[2-Chloro-4-isopropylphenyl]-2-cyano-3-methyl-pent-2,4-dienoic acid ethyl ester A mixture of 4-(2-chloro-4-isopropylphenyl)but-3-en-2-one (50 mmol), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part B: 2-Amino-4-[2-(2-chloro-4-isopropylphenyl)vinyl]-thiophene-3-carboxylic acid ethyl ester The mixture of E and Z-isomers of 5-[2-chloro-4-isopropylphenyl]-2-cyano-3-methyl-pent-2,4-dienoic acid ethyl ester (39.5 mmol, Example 31, Part A), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part C: 4-[2-(2-Chloro-4-isopropylphenyl)vinyl]-2-(1,3-dioxo-1,3-dihydroisoindol-2-yl)-thiophene-3-carboxylic acid ethyl ester A mixture of 2-amino-4-[2-(2-chloro-4-isopropylphenyl)vinyl]-thiophene-3-carboxylic acid ethyl ester (2 mmol, Example 31, Part B) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part D: 4-[2-(2-Chloro-4-isopropylphenyl)vinyl]-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-[2-(2-chloro-4-isopropylphenyl)vinyl]-2-(1,3-dioxo-1,3-dihydroisoindol-2-yl)-thiophene-3-carboxylic acid ethyl ester (0.7 mmol, Example 31, Part C). The mixture is heated to reflux for 90 min, then diluted with water (12 mL), chilled in an ice bath, and acidified with concentrated HCl. The product that precipitates is collected by filtration, washed with water, and dried, affording the desired compound.

Part E: 8-Chloro-3-(1,3-dioxo-1,3-dihydroisoindol-2-yl)-6-isopropyl-2-thia-benzo[f]azulen-4-one A suspension of 4-[2-(2-chloro-4-isopropylphenyl)vinyl]-2-(1,3-dioxo-1,3-dihydroisoindol-2-yl)-thiophene-3-carboxylic acid (1.15 mmol, Example 31, Part D) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part F: 3-Amino-8-chloro-6-isopropyl-2-thia-benzo[f]azulen-4-one. [Formula (IV): $R^2=CH(CH_3)_2$; $R^4=Cl$; $R^1=R^3=R^5=R^6=R^7=H$; $R^9+R^{10}=O$]

To a suspension of Part E: 8-chloro-3-(1,3-dioxo-1,3-dihydroisoindol-2-yl)-6-isopropyl-2-thia-benzo[f]azulen-4-one (0.45 mmol, Example 30, Part E) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 32

Part A: Diethyl 2-acetyl-2-phenylmalonate

To a solution of diethyl 2-phenylmalonate (100 mmol) in anhydrous tetrahydrofuran (300 mL) is added sodium ethoxide (110 mmol). The mixture is stirred at room temperature for 30 min, followed by the addition of a solution of acetyl chloride (110 mmol) in tetrahydrofuran (50 mL). After the addition is complete, the mixture is heated to reflux for 3 hours, cooled to room temperature, neutralized with 2 N HCl, then concentrated in vacuo. The residue is partitioned between $H_2O$ and $CHCl_3$, the organic extracts washed with sodium bicarbonate, water, and brine, dried ($MgSO_4$), filtered and concentrated.

Part B: 2-Cyano-4,4-bis(ethoxycarbonyl)-3-methyl-4-phenyl-but-2-enoic acid ethyl ester A mixture of diethyl 2-acetyl-2-phenylmalonate (50 mmol, Example 32, Part A), ethyl cyanoacetate (50 mmol), acetic acid (1.14 mL) ammonium acetate (400 mg), and benzene (50 mL) is heated to reflux in a Dean-Stark apparatus. After approximately 10 hours, additional ethyl cyanoacetate (50 mmol), acetic acid (1.14 mL), and ammonium acetate (400 mg) are added. After an additional 10 hours, the reaction is cooled to room temperature, diluted with ethyl acetate (30 mL), washed with water (240 mL), brine (40 mL), and dried ($Na_2SO_4$). After filtering, the extract is concentrated in vacuo and the desired product, as a mixture of E and Z-isomers, is isolated by column chromatography on silica gel, eluting with 5% ethyl acetate in petroleum ether.

Part C: 2-Amino-4-(α,α-(bis-ethoxycarbonyl)benzyl)-thiophene-3-carboxylic acid ethyl ester The mixture of E and Z-isomers of 2-cyano-4,4-bis(ethoxycarbonyl)-3-methyl-4 phenyl-but-2-enoic acid ethyl ester (39.5 mmol, Example 32, Part B), morpholine (39.5 mmol), and sulfur (39.5 mmol) in ethanol (100 mL) is heated to reflux for 1.5-3.0 hours. After cooling to room temperature, the mixture is concentrated in vacuo and the residue dissolved in ethyl acetate (30 mL). After washing with water (15 mL) and brine (15 mL), the organic layers are dried ($Na_2SO_4$), filtered, and concentrated. The residue is chromatographed on a column of silica gel to afford the desired product.

Part D: 2-Amino-4-benzyl-thiophene-3-carboxylic acid

A solution of 2-amino-4-(α,α-(bis-ethoxycarbonyl)benzyl)-thiophene-3-carboxylic acid ethyl ester (10 mmol, Example 32, Part C) in dimethylsulfoxide (50 mL) is added sodium hydride (21 mmol), followed by the cautious addition of water (21 mmol). The mixture is heated to 160° C. for 6 hours, cooled to room temperature, diluted with water (100 mL), neutralized with HCl, and extracted with ethyl acetate. The organic extract is repeatedly washed with water, dried, filtered and concentrated. The residue is purified by column chromatography on silica gel.

Part E: 4-Benzyl-2-(1,3-dioxo-1,3-dihydroisoindol-2-yl)-thiophene-3-carboxylic acid ethyl ester A mixture of 2-amino-4-benzyl-thiophene-3-carboxylic acid ethyl ester (2 mmol, Example 32, Part D) and phthalic anhydride (2.2 mmol) in glacial acetic acid (20 mL) is heated at reflux overnight. After cooling to room temperature, the acetic acid is removed in vacuo and the residue triturated with petroleum ether. The crude product is collected by filtration, suspended in acetyl chloride (5 mL), and heated to reflux for one hour. After removing the solvent in vacuo, the residue is dissolved in ethyl acetate (30 mL), washed sequentially with 5% aqueous $NaHCO_3$ (10 mL), water (10 mL), brine (10 mL), dried ($Na_2SO_4$), filtered, and concentrated in vacuo. Recrystallization affords the desired product.

Part F: 4-Benzyl-2-(1,3-dioxo-1,3-dihydroisoindol-2-yl)-thiophene-3-carboxylic acid To a solution of NaOH (1.4 mmol) in a 1:1 mixture of methanol:$H_2O$ (6 mL) is added 4-benzyl-2-(1,3-dioxo-1,3-dihydroisoindol-2-yl)-thiophene-3-carboxylic acid ethyl ester (0.7 mmol, Example 32, Part E). The mixture is heated to reflux for 90 min, then diluted with water (12 mL), chilled in an ice bath, and acidified with concentrated HCl. The product that precipitates is collected by filtration, washed with water, and dried, affording the desired compound.

Part G: 2-[4-Oxo-9H-naphtho[2,3-c]thiophene-3-yl]-isoindole-1,3-dione

A suspension of 4-benzyl-2-(1,3-dioxo-1,3-dihydroisoindol-2-yl)-thiophene-3-carboxylic acid (1.15 mmol, Example 32, Part F) in thionyl chloride (3 mL) is heated to reflux for 30 min, providing a homogeneous solution. The mixture is concentrated to afford the crude acid chloride, then co-evaporated with four successive aliquots of benzene to remove the last traces of thionyl chloride, providing the acid chloride.

The crude acid chloride, dissolved in anhydrous methylene chloride (3 mL), is added to a suspension of anhydrous aluminum chloride (4.60 mmol) in anhydrous methylene chloride (5 mL). The resulting mixture is heated to reflux for three hours, cooled to room temperature, and poured onto a mixture of 1 M HCl (20 mL) and ice. The organic layer is collected and the aqueous layer extracted with additional methylene chloride (2×10 mL). The combined organic layers are washed with water (10 mL), brine (10 mL), dried ($Na_2SO_4$), filtered, and concentrated. The residue is applied to a short column of silica gel, eluting with ethyl acetate, to afford the desired product.

Part H: 3-Amino-9H-naphtho[2,3-c]thiophene-4-one. [Formula (II): $R^1=R^2=R^3=R^4=R^5=R^6=R^7=R^8=H$; $R^9+R^{10}=O$]

To a suspension of 2-[4-oxo-9H-naphtho[2,3-c]thiophene-3-yl]-isoindole-1,3-dione (0.45 mmol, Example 32, Part G) in absolute ethanol (5 mL) is added hydrazine hydrate (0.5 mmol). The mixture is heated to reflux for one hour, cooled to room temperature, concentrated in vacuo, and the residue dissolved in methylene chloride. The solution is chilled to 5° C. for one hour, during which time the phthaloyl hydrazide precipitates. The precipitate is removed by filtration, the filtrate concentrated in vacuo, and the residue purified by column chromatography on silica gel, eluting with a 4:1 mixture of petroleum ether:ethyl acetate. Fractions containing the product are collected, evaporated, and the product recrystallized.

EXAMPLE 33

Pharmaceutical Formulations

| (A) Transdermal System-for 1000 patches | |
|---|---|
| Ingredients | Amount |
| Active compound | 100 g |
| Silicone fluid | 450 g |
| Colloidal silicon dioxide | 2 g |

The silicone fluid and active compound are mixed together and the colloidal silicone dioxide is added to increase viscosity. The material is then dosed into a subsequent heat sealed polymeric laminate comprised of the following: polyester release liner, skin contact adhesive composed of silicone or acrylic polymers, a control membrane which is a polyolefin, and an impermeable backing membrane made of a polyester multilaminate. The resulting laminated sheet is than cut into 10 sq. cm patches.

| (B) Oral Tablet-For 1000 Tablets | |
|---|---|
| Ingredients | Amount |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| (C) Injection-for 1000, 1 mL Ampules | |
|---|---|
| Ingredients | Amount |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

| (D) Continuous Injection-for 1000 mL | |
|---|---|
| Ingredients | Amount |
| Active compound | 10 g |
| Buffering Agents | q.s. |
| Water for injection | q.s. 1000 mL |

EXAMPLE 34

Measurement of cAMP Enhancement in CHO Cells

Chinese hamster ovary cells expressing human recombinant $A_1$-adenosine receptors (CHO:huA1 cells) at a density of approximately 8000 fmol/mg protein were prepared as previously described (Kollias-Baker et al., (1997), *J. Pharmacol. Exp. Ther.* 281: 761-768) and aliquots of the cells at low passage numbers were frozen and stored in liquid nitrogen. When compounds were tested, an aliquot of CHO:huA1 cells were rapidly thawed after removal from liquid nitrogen, then grown in Ham's F12 culture medium with 10% fetal bovine serum and 0.5 mg/mL of antibiotic G-418 (Shryock, Ozeck, and Belardinelli (1998), *Mol. Pharmacol.* 53: 886-893). Cells were passaged thrice weekly. Aliquots of cells were placed into 12-well plates with culture medium, serum, and antibiotic for 48 hours, by which time the cells had grown to a confluent monolayer.

Allosteric enhancement was measured as the action of a test compound at different concentrations (0.01, 0.1, 1 and 10 µM) to reduce the cAMP content of CHO:huA1 cells. To initiate an experiment, growth medium was removed from the 12-well plates and cells were washed once with warm Hanks' buffered saline. The wash solution was then removed and replaced with fresh Hanks' solution containing forskolin (1 µM), rolipram (20 µM), $N^6$-cyclopentyladenosine (CPA, 0.01 nM), adenosine deaminase (2 U/mL), and the test compound. Forskolin was used to stimulate the activity of adenylyl cyclase, rolipram to inhibit cAMP phosphodiesterase, adenosine deaminase to degrade endogenous adenosine, and CPA to cause a small increase of the number of activated adenosine receptors. After 6 min of incubation at 36° C. in the presence of test compound, the incubation solution was removed and hydrochloric acid (final concentration 50 mM) was added to terminate drug action. The content of cAMP in acidified extracts of cells was determined by radioimmunoassay as previously described (Kollias-Baker et al., (1997), *J. Pharmacol. Exp. Ther.* 281: 761-768). Because the magnitude of the effects of allosteric enhancers on CHO:huA1 cells changed subtly with passage number and differed slightly among different aliquots of cells, the actions of the test compounds and the action of a reference compound (PD 81,723) were assessed in each experiment. The effect of each test compound on cAMP content is presented in the accompanying table as a percentage of the value of cAMP content in the absence of drug (control, 100%). Each value is a mean±standard error of 6 determinations in each of the number of experiments indicated in the "n" column of the table.

TABLE 1

Percentage Change in cAMP Content of CHO Cells in Presence of Test Compounds

| | | Change in cAMP Content from Control (Mean ± SEM) Concentration of Test Compound | | | |
|---|---|---|---|---|---|
| Example | N | 0.01 µM | 0.1 µM | 1 µM | 10 µM |
| 21 | 3 | −5 ± 4 | −15 ± 2 | 4 ± 5 | −16 ± 3 |
| 22 | 3 | 4 ± 2 | −1 ± 8 | 0 ± 7 | −17 ± 2 |
| 23 | 3 | −7 ± 2 | 9 ± 9 | −16 ± 3 | −42 ± 1 |
| 24 | 3 | 5 ± 3 | 5 ± 3 | −1 ± 1 | −23 ± 6 |
| 25 | 3 | 0 ± 5 | −9 ± 8 | −46 ± 2 | −75 ± 3 |
| 26 | 3 | −4 ± 1 | −1 ± 7 | 15 ± 6 | 25 ± 7 |
| 27 | 3 | 6 ± 3 | 8 ± 5 | 8 ± 9 | 0 ± 9 |
| PD 81,72 | 3 | 4 ± 2 | 8 ± 3 | −32 ± 2 | −75 ± 1 |

The invention has been described in detail with reference to preferred embodiments thereof. However, it will be appreciated that those skilled in the art, upon consideration of the disclosure, may make modifications and improvements within the spirit and scope of the invention.

TABLE 2

Preferred compounds of the invention

| No. | Chemical name | Structure |
|---|---|---|
| (1) | 1-amino-8H-indeno[2,1-c]thiophen-8-one | 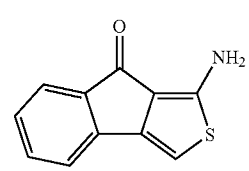 |
| (2) | 1-amino-5-chloro-8H-indeno[2,1-c]thiophen-8-one | 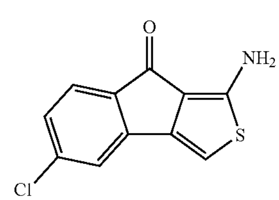 |

TABLE 2-continued

Preferred compounds of the invention

| No. | Chemical name | Structure |
|---|---|---|
| (3) | 1-amino-5-methyl-8H-indeno[2,1-c]thiophen-8-one | 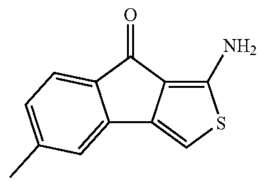 |
| (4) | 1-amino-4,5-dichloro-8H-indeno[2,1-c]thiophen-8-one | 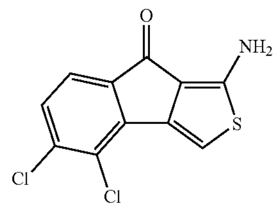 |
| (5) | 1-amino-4,5-dimethyl-8H-indeno[2,1-c]thiophen-8-one | 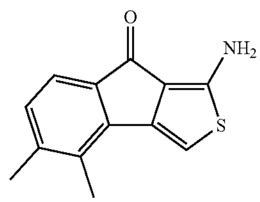 |
| (6) | 1-amino-5-ethyl-8H-indeno[2,1-c]thiophen-8-one | 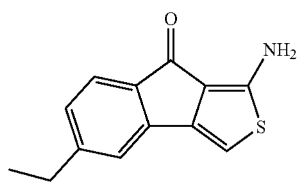 |
| (7) | 1-amino-5-propyl-8H-indeno[2,1-c]thiophen-8-one | 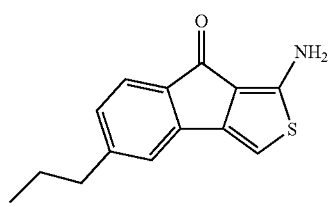 |
| (8) | 1-amino-7-methyl-8H-indeno[2,1-c]thiophen-8-one | 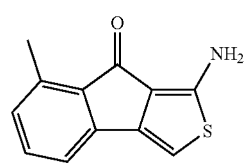 |
| (9) | 1-amino-7-chloro-8H-indeno[2,1-c]thiophen-8-one | 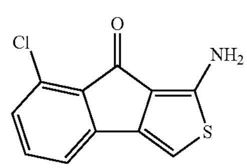 |
| (10) | 1-amino-6,7-dichloro-8H-indeno[2,1-c]thiophen-8-one | 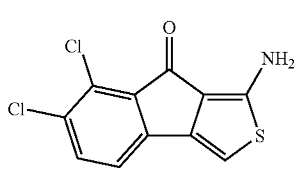 |

TABLE 2-continued

Preferred compounds of the invention

| No. | Chemical name | Structure |
|---|---|---|
| (11) | 1-amino-5,6-dichloro-8H-indeno[2,1-c]thiophen-8-one | 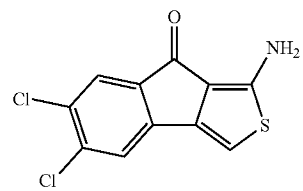 |
| (12) | 1-amino-4-chloro-8H-indeno[2,1-c]thiophen-8-one | 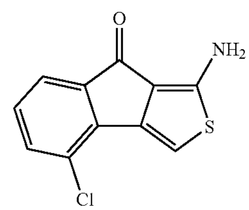 |
| (13) | 1-amino-6-chloro-8H-indeno[2,1-c]thiophen-8-one | 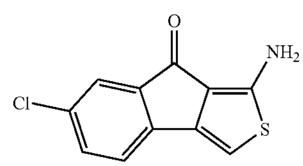 |
| (14) | 1-amino-4-methyl-8H-indeno[2,1-c]thiophen-8-one | 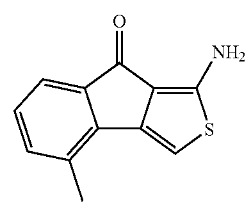 |
| (15) | 1-amino-6-methyl-8H-indeno[2,1-c]thiophen-8-one | 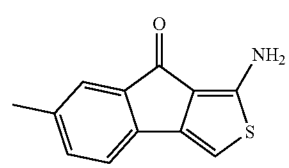 |
| (16) | 1-amino-6-ethyl-8H-indeno[2,1-c]thiophen-8-one | 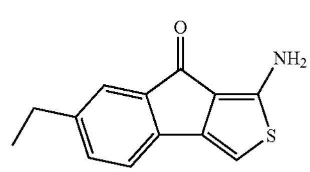 |
| (17) | 1-amino-4-methoxy-8H-indeno[2,1-c]thiophen-8-one | 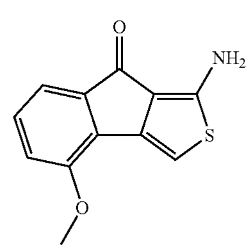 |

TABLE 2-continued

Preferred compounds of the invention

| No. | Chemical name | Structure |
|---|---|---|
| (18) | 1-amino-5-methoxy-8H-indeno[2,1-c]thiophen-8-one | 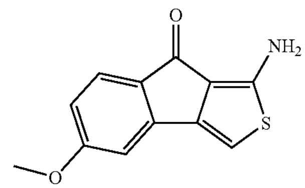 |
| (19) | 1-amino-7-methoxy-8H-indeno[2,1-c]thiophen-8-one | 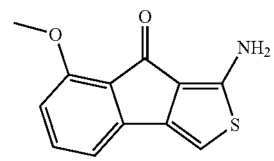 |
| (20) | 1-amino-6-methoxy-8H-indeno[2,1-c]thiophen-8-one | 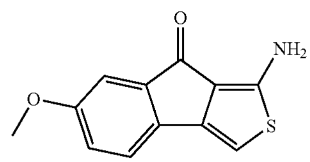 |
| (21) | 1,6-diamino-8H-indeno[2,1-c]thiophen-8-one | 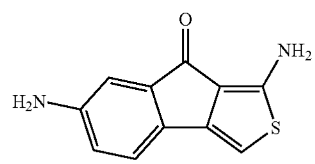 |
| (22) | 3-amino-naphtho[2,3-c]thiophen-4(9H)-one | 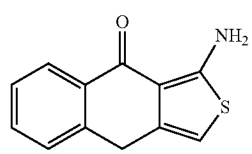 |
| (23) | 3-amino-6-chloro-naphtho[2,3-c]thiophen-4(9H)-one | 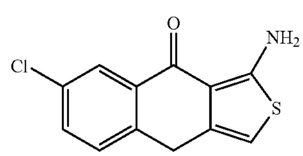 |
| (24) | 3-amino-6-methyl-naphtho[2,3-c]thiophen-4(9H)-one | 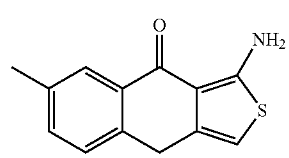 |
| (25) | 3-amino-6,7-dichloro-naphtho[2,3-c]thiophen-4(9H)-one | 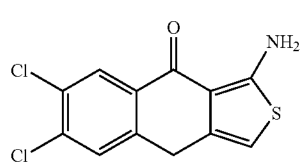 |
| (26) | 3-amino-6,7-dimethyl-naphtho[2,3-c]thiophen-4(9H)-one | 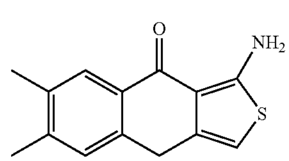 |

TABLE 2-continued

Preferred compounds of the invention

| No. | Chemical name | Structure |
|---|---|---|
| (27) | 3-amino-6-ethyl-naphtho[2,3-c]thiophen-4(9H)-one | 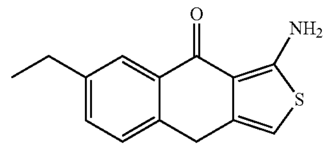 |
| (28) | 3-amino-6-propyl-naphtho[2,3-c]thiophen-4(9H)-one | 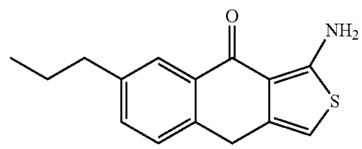 |
| (29) | 3-amino-8-chloro-naphtho[2,3-c]thiophen-4(9H)-one | 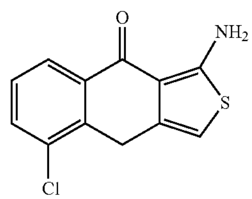 |
| (30) | 5-amino-2-benzyl-1,2,3,10b-tetrahydro-6H-benzo[h]thieno[2,3,4-de]isoquinolin-6-one | 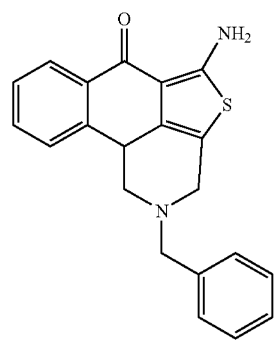 |
| (31) | 5-amino-2-benzyl-9-chloro-1,2,3,10b-tetrahydro-6H-benzo[h]thieno[2,3,4-de]isoquinolin-6-one | 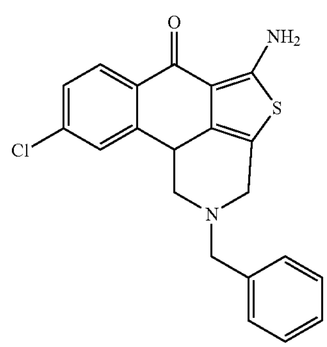 |
| (32) | 5-amino-2-benzyl-9-methyl-1,2,3,10b-tetrahydro-6H-benzo[h]thieno[2,3,4-de]isoquinolin-6-one | 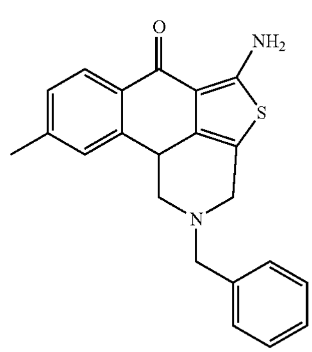 |

TABLE 2-continued

Preferred compounds of the invention

| No. | Chemical name | Structure |
|---|---|---|
| (33) | 5-amino-2-benzyl-8,9-dichloro-1,2,3,10b-tetrahydro-6H-benzo[h]thieno[2,3,4-de]isoquinolin-6-one | 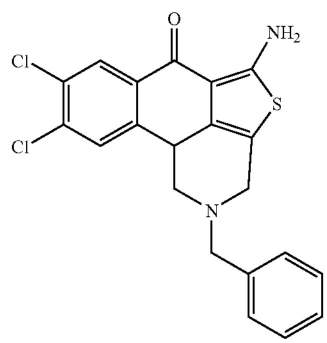 |
| (34) | 5-amino-2-benzyl-8,9-dimethyl-1,2,3,10b-tetrahydro-6H-benzo[h]thieno[2,3,4-de]isoquinolin-6-one | 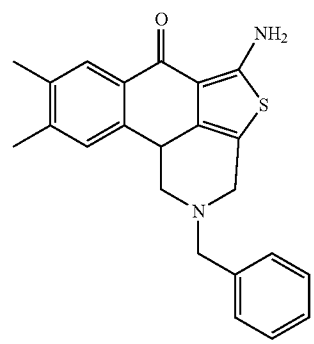 |
| (35) | 5-amino-2-benzyl-9-ethyl-1,2,3,10b-tetrahydro-6H-benzo[h]thieno[2,3,4-de]isoquinolin-6-one | 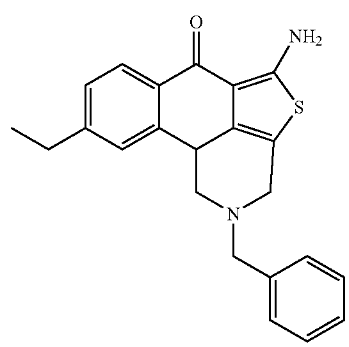 |
| (36) | 5-amino-2-benzyl-9-propyl-1,2,3,10b-tetrahydro-6H-benzo[h]thieno[2,3,4-de]isoquinolin-6-one | 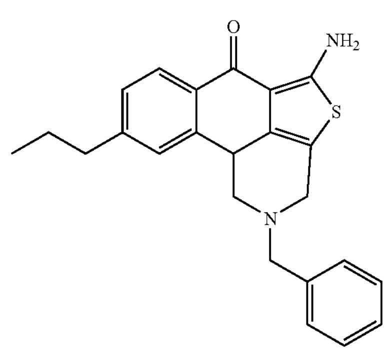 |

TABLE 2-continued

Preferred compounds of the invention

| No. | Chemical name | Structure |
|---|---|---|
| (37) | 5-amino-2-benzyl-10b-methyl-1,2,3,10b-tetrahydro-6H-benzo[h]thieno[2,3,4-de]isoquinolin-6-one | 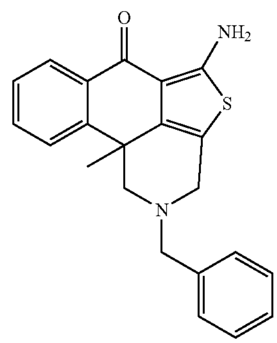 |
| (38) | 5-amino-2-benzyl-9-chloro-10b-methyl-1,2,3,10b-tetrahydro-6H-benzo[h]thieno[2,3,4-de]isoquinolin-6-one | 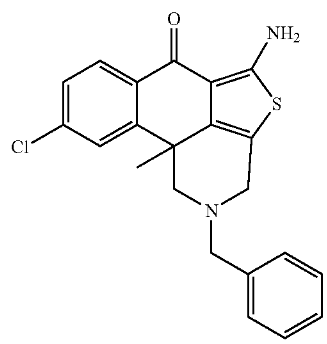 |
| (39) | 5-amino-2-benzyl-9,10b-dimethyl-1,2,3,10b-tetrahydro-6H-benzo[h]thieno[2,3,4-de]isoquinolin-6-one | 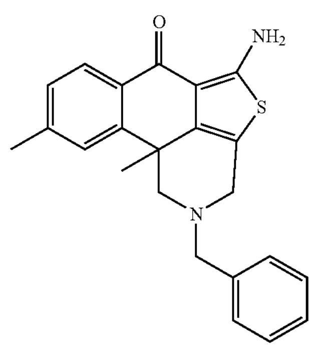 |
| (40) | 5-amino-2-benzyl-8,9-dichloro-10b-methyl-1,2,3,10b-tetrahydro-6H-benzo[h]thieno[2,3,4-de]isoquinolin-6-one | 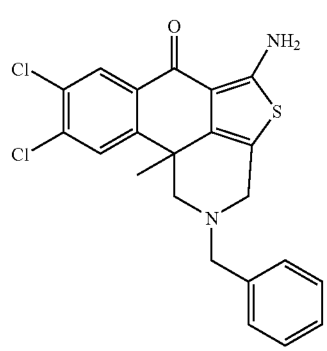 |

TABLE 2-continued

Preferred compounds of the invention

| No. | Chemical name | Structure |
|---|---|---|
| (41) | 5-amino-2-benzyl-8,9,10b-trimethyl-1,2,3,10b-tetrahydro-6H-benzo[h]thieno[2,3,4-de]isoquinolin-6-one | 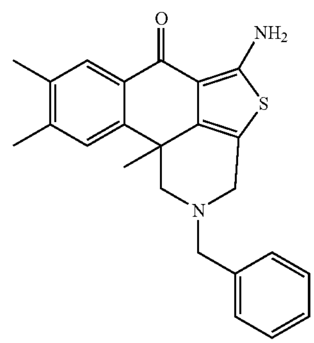 |
| (42) | 5-amino-2-benzyl-9-ethyl-10b-methyl-1,2,3,10b-tetrahydro-6H-benzo[h]thieno[2,3,4-de]isoquinolin-6-one | 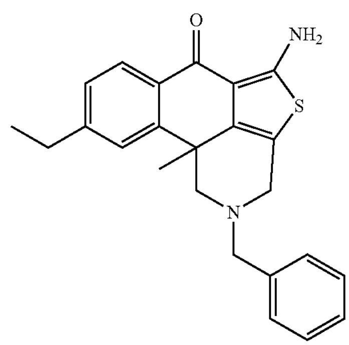 |
| (43) | 5-amino-2-benzyl-9-propyl-10b-methyl-1,2,3,10b-tetrahydro-6H-benzo[h]thieno[2,3,4-de]isoquinolin-6-one | 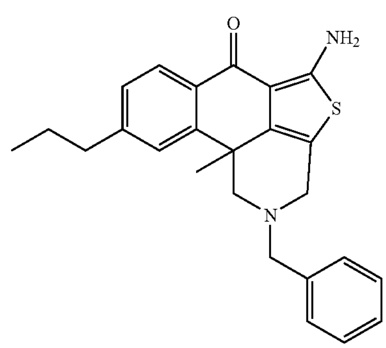 |
| (44) | 1-amino-4-benzyl-4,5,5a,6-tetrahydro-2-thia-4-azadibenzo[cd,g]azulen-11(3H)-one | 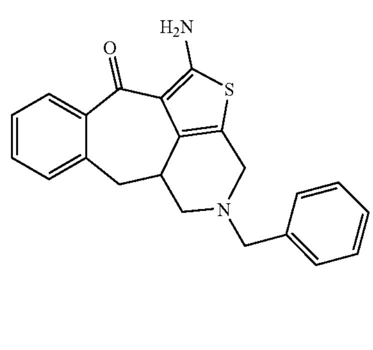 |

TABLE 2-continued

Preferred compounds of the invention

| No. | Chemical name | Structure |
|---|---|---|
| (45) | 1-amino-4-benzyl-8-chloro-4,5,5a,6-tetrahydro-2-thia-4-azadibenzo[cd,g]azulen-11(3H)-one | 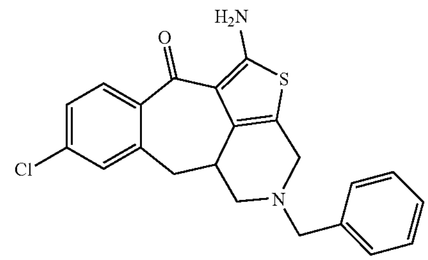 |
| (46) | 1-amino-4-benzyl-8-methyl-4,5,5a,5-tetrahydro-2-thia-4-azadibenzo[cd,g]azulen-11(3H)-one | 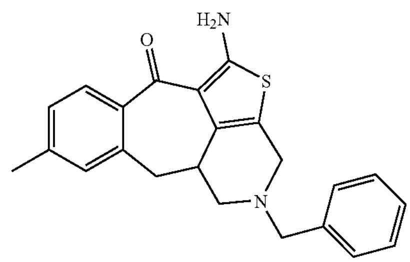 |
| (47) | 1-amino-4-benzyl-8,9-dichloro-4,5,5a,6-tetrahydro-2-thia-4-azadibenzo[cd,g]azulen-11(3H)-one | 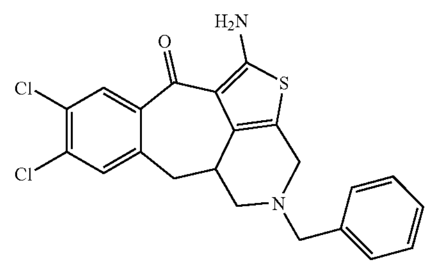 |
| (48) | 1-amino-4-benzyl-8,9-dimethyl-4,5,5a,6-tetrahydro-2-thia-4-azadibenzo[cd,g]azulen-11(3H)-one | 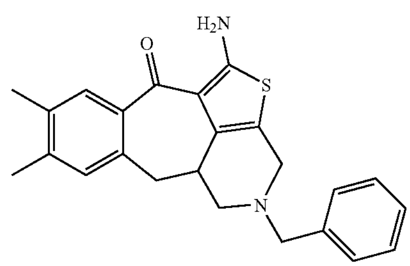 |
| (49) | 1-amino-4-benzyl-8-ethyl-4,5,5a,6-tetrahydro-2-thia-4-azadibenzo[cd,g]azulen-11(3H)-one | 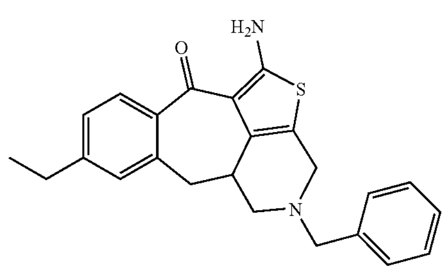 |

TABLE 2-continued

Preferred compounds of the invention

| No. | Chemical name | Structure |
|---|---|---|
| (50) | 1-amino-4-benzyl-8-propyl-4,5,5a,6-tetrahydro-2-thia-4-azadibenzo[cd,g]azulen-11(3H)-one | 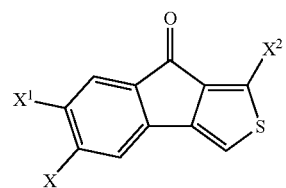 |

What is claimed is:

1. A method of treating chronic pain in a mammal which method comprises administering to a mammal, in need thereof, a therapeutically effective amount of a fused thiophene compound of the Formula:

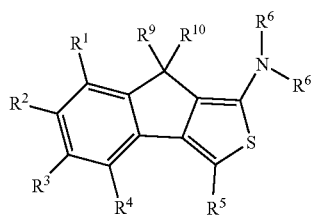

Formula (I)

wherein $R^1$, $R^2$, $R^3$, and $R^4$ are independently hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted alkylthio, optionally substituted alkylsulfinyl, optionally substituted alkylsulfonyl, optionally substituted alkanoyl, optionally substituted carbocyclic aryl, or an optionally substituted heteroalicyclic or heteroaromatic;

$R^5$ is hydrogen, optionally substituted alkyl, optionally substituted alkenyl, optionally substituted alkynyl, optionally substituted carbocyclic aryl, or an optionally substituted heteroalicyclic or heteroaromatic;

each $R^6$ is hydrogen;

$R^9$ and $R^{10}$ are independently hydrogen or hydroxyl, or together may represent a carbonyl oxygen;

wherein said heteroalicyclic is a monovalent saturated or unsaturated carbocyclic group having a single ring or multiple condensed rings, from 1 to 15 carbon atoms and from 1 to 5 heteroatoms within the ring or rings selected from the group of heteroatoms consisting of nitrogen, sulfur, and oxygen;

wherein said heteroaromatic is a 5-membered or 6-membered heterocyclic, aromatic group, which can optionally be fused to an aryl or substituted aryl ring or fused to a second or third heteroaromatic group;

or a pharmaceutically acceptable salt thereof.

2. The method according to claim 1 wherein the chronic pain is neuropathic pain.

3. The method according to claim 2 wherein the mammal is a human.

4. The method according to claim 1 wherein the fused thiophene compound of Formula (I) is having the Formula:

Formula (V)

wherein

X and $X^1$ are independently H, optionally substituted alkyl, optionally substituted alkenyl, optionally substituted alkynyl, optionally substituted alkoxy, optionally substituted carbocyclic aryl, nitro or halogen, $X^2$ is amino;

or a pharmaceutically acceptable salt thereof.

5. The method according to claim 4 wherein the chronic pain is neuropathic pain.

6. The method according to claim 5 wherein the mammal is a human.

7. The method according to claim 1 wherein the fused thiophene compound of Formula (I) is selected from the group consisting of:

1-amino-8H-indeno[1,2-c]thiophen-8-one;
1-amino-5-chloro-8H-indeno[1,2-c]thiophen-8-one;
1-amino-5-methyl-8H-indeno[1,2-c]thiophen-8-one;
1-amino-4,5-dichloro-8H-indeno[1,2-c]thiophen-8-one;
1-amino-4,5-dimethyl-8H-indeno[1,2-c]thiophen-8-one;
1-amino-5-ethyl-8H-indeno[1,2-c]thiophen-8-one;
1-amino-5-propyl-8H-indeno[1,2-c]thiophen-8-one;
1-amino-7-methyl-2-thia-cyclopenta[a]inden-8-one;
1-amino-7-chloro-2-thia-cyclopenta[a]inden-8-one;
1-amino-6,7-dichloro-2-thia-cyclopenta[a]inden-8-one;
1-amino-5,6-dichloro-2-thia-cyclopenta[a]inden-8-one;
1-amino-4-chloro-2-thia-cyclopenta[a]inden-8-one;
1-amino-6-chloro-2-thia-cyclopenta[a]inden-8-one;
1-amino-4-methyl-2-thia-cyclopenta[a]inden-8-one;
1-amino-6-methyl-2-thia-cyclopenta[a]inden-8-one;
1-amino-6-ethyl-2-thia-cyclopenta[a]inden-8-one;
1-amino-4-methoxy-2-thia-cyclopenta[a]inden-8-one;
1-amino-5-methoxy-2-thia-cyclopenta[a]inden-8-one;

1-amino-7-methoxy-2-thia-cyclopenta[a]inden-8-one;
1-amino-6-methoxy-2-thia-cyclopenta[a]inden-8-one; and
1,6-diamino-2-thia-cyclopenta[a]inden-8-one;
or a pharmaceutically acceptable salt thereof.

8. The method according to claim 7 wherein the chronic pain is neuropathic pain.

9. The method according to claim 8 wherein the mammal is a human.

* * * * *

UNITED STATES PATENT AND TRADEMARK OFFICE
CERTIFICATE OF CORRECTION

PATENT NO. : 7,449,490 B2  Page 1 of 1
APPLICATION NO. : 11/402240
DATED : November 11, 2008
INVENTOR(S) : Moorman et al.

It is certified that error appears in the above-identified patent and that said Letters Patent is hereby corrected as shown below:

Column 26, lines 30 and 46; column 27, lines 6, 19 and 27; column 28, lines 25 and 41; column 29, lines 24, 34 and 41; column 30, lines 38 and 54; column 31, lines 38, 49 and 55; column 32, line 53; column 33, lines 3 and 60; column 34, lines 4 and 12; column 35, line 46; column 37, line 17; column 38, line 61; column 40, line 35; column 42, line 5; column 43, line 48; column 45, line 34; column 47, line 11; column 48, line 50; column 50, line 34; column 52, line 5; column 53, line 47; column 54, lines 16 and 34; column 56, lines 5 and 63; column 58, lines 38, 52, 54, 60 and 62; column 60, line 50; column 62, line 36; column 64, line 12; column 65, line 8; and column 66, line 11; in each instance, "C." should be changed to --C--.

Column 1, line 67 continuing to column 2, line 1, "signif cant" should be changed to --significant--.

Column 5, lines 23 and 26, in each instance, "increase" should be changed to --decrease--.

Column 25, line 52, "$Na_2S0_4$" should be changed to --$Na_2SO_4$--.

Column 28, line 66, "Na2SO4" should be changed to --$Na_2SO_4$--.

Column 29, line 64, "temperature" should be changed to --temperature.--.

Signed and Sealed this

Thirteenth Day of July, 2010

David J. Kappos
*Director of the United States Patent and Trademark Office*